United States Patent
Radmand

(10) Patent No.: US 12,403,033 B2
(45) Date of Patent: Sep. 2, 2025

(54) ORAL APPLIANCE FOR THE TREATMENT OF SLEEP APNEA

(71) Applicant: Achaemenid, LLC, Stratford, CT (US)

(72) Inventor: Reza Radmand, Boston, MA (US)

(73) Assignee: Achaemenid, LLC, Boston, MA (US)

( * ) Notice: Subject to any disclaimer, the term of this patent is extended or adjusted under 35 U.S.C. 154(b) by 0 days.

(21) Appl. No.: 18/514,966

(22) Filed: Nov. 20, 2023

(65) Prior Publication Data

US 2024/0350298 A1 Oct. 24, 2024

Related U.S. Application Data

(63) Continuation-in-part of application No. 18/209,298, filed on Jun. 13, 2023, now abandoned.

(60) Provisional application No. 63/497,605, filed on Apr. 21, 2023.

(51) Int. Cl.
| | |
|---|---|
| A61F 5/56 | (2006.01) |
| A61B 5/00 | (2006.01) |
| A61B 5/145 | (2006.01) |
| A61B 5/1455 | (2006.01) |
| A61B 5/256 | (2021.01) |

(52) U.S. Cl.
CPC .......... A61F 5/566 (2013.01); A61B 5/14546 (2013.01); A61B 5/14552 (2013.01); A61B 5/256 (2021.01); A61B 5/4848 (2013.01)

(58) Field of Classification Search
CPC .... A61B 5/145; A61B 5/14546–14552; A61B 5/24; A61B 5/25; A61B 5/251; A61B 5/256; A61B 5/48; A61B 5/4806–4818; A61B 5/4848; A61C 7/08; A61C 7/36; A63B 71/085; A61F 5/56–566
See application file for complete search history.

(56) References Cited

U.S. PATENT DOCUMENTS

| | | | |
|---|---|---|---|
| 3,599,629 A | 8/1971 | Gordy | |
| 4,629,424 A | 12/1986 | Lauks et al. | |
| 4,777,954 A | 10/1988 | Keusch et al. | |
| 5,190,053 A | 3/1993 | Meer | |
| 5,203,329 A * | 4/1993 | Takatani | A61B 5/14552 |
| | | | 356/41 |
| 5,212,476 A | 5/1993 | Maloney | |

(Continued)

FOREIGN PATENT DOCUMENTS

| | | |
|---|---|---|
| AU | 2002100414 B4 | 11/2002 |
| CN | 1823691 A | 8/2006 |

(Continued)

OTHER PUBLICATIONS

US 10,350,107 B2, 07/2019, Kopelman (withdrawn)

(Continued)

*Primary Examiner* — Michelle J Lee
(74) *Attorney, Agent, or Firm* — Womble Bond Dickinson (US) LLP

(57) ABSTRACT

An oral appliance may include a mouthpiece configured to be positioned in an oral cavity of a user and an electronic assembly coupled to the mouthpiece. The electronic assembly may include an oxygen sensor oriented toward soft tissue of the user's mouth to determine an oxygen saturation level of the user. The electronic assembly may be positioned within an appendage extending away from a wall of the mouthpiece.

20 Claims, 29 Drawing Sheets

(56) References Cited

U.S. PATENT DOCUMENTS

| | | |
|---|---|---|
| 5,284,161 A | 2/1994 | Karell |
| 5,490,520 A | 2/1996 | Schaefer et al. |
| 5,765,563 A | 6/1998 | Vander Schaaf |
| 5,792,067 A | 8/1998 | Karell |
| 6,212,435 B1 | 4/2001 | Lattner et al. |
| 6,263,223 B1 | 7/2001 | Shepherd et al. |
| 6,418,933 B1 | 7/2002 | Strong |
| 6,471,716 B1 | 10/2002 | Pecukonis |
| 6,536,439 B1 | 3/2003 | Palmisano |
| 6,598,006 B1 | 7/2003 | Honda et al. |
| 6,604,527 B1 | 8/2003 | Palmisano |
| 7,216,648 B2 | 5/2007 | Nelson et al. |
| 7,690,378 B1 | 4/2010 | Turcott |
| 7,711,438 B2 | 5/2010 | Lattner et al. |
| 7,754,345 B2 | 7/2010 | Tsai |
| 7,885,708 B2 | 2/2011 | Shanks et al. |
| 8,701,672 B2 | 4/2014 | Vaska |
| 8,751,005 B2 | 6/2014 | Meadows et al. |
| D718,448 S | 11/2014 | Bedford et al. |
| D718,449 S | 11/2014 | Bedford et al. |
| 10,195,426 B2 | 2/2019 | Kent et al. |
| 10,195,427 B2 | 2/2019 | Kent et al. |
| 10,206,570 B2 | 2/2019 | McKenna et al. |
| 10,219,935 B2 | 3/2019 | Hadas |
| 10,244,982 B2 | 4/2019 | Radmand et al. |
| 10,251,774 B2 | 4/2019 | Shah et al. |
| 10,376,202 B2 | 8/2019 | Shah et al. |
| 10,376,210 B2 | 8/2019 | Paris et al. |
| 10,420,672 B2 | 9/2019 | Hermanson et al. |
| 10,470,921 B2 | 11/2019 | Radmand |
| 10,674,960 B2 | 6/2020 | Fridman |
| 10,716,701 B2 | 7/2020 | Heer et al. |
| 10,862,508 B1 | 12/2020 | Zhao et al. |
| 10,874,542 B2 | 12/2020 | Hermanson et al. |
| 10,945,665 B1 | 3/2021 | Tran et al. |
| 11,000,405 B2 | 5/2021 | Radmand |
| 11,033,750 B1 | 6/2021 | Radmand |
| 11,141,592 B2 | 10/2021 | Scheiner |
| 11,191,663 B2 | 12/2021 | Radmand |
| 11,234,638 B2 | 2/2022 | Radmand |
| 11,304,778 B2 | 4/2022 | Shanjani et al. |
| 11,375,951 B2* | 7/2022 | Radmand .............. A63B 71/085 |
| 11,432,768 B2 | 9/2022 | Fridman |
| 11,464,451 B1* | 10/2022 | Zavanelli .............. A61B 5/6833 |
| 11,786,177 B2* | 10/2023 | Radmand .............. A61B 5/4818 |
| | | 600/383 |
| 2001/0034068 A1 | 10/2001 | Spivey et al. |
| 2003/0154990 A1 | 8/2003 | Parker |
| 2005/0113654 A1 | 5/2005 | Weber et al. |
| 2006/0207611 A1 | 9/2006 | Anonsen |
| 2007/0046461 A1 | 3/2007 | Radmand |
| 2007/0173893 A1 | 7/2007 | Pitts |
| 2008/0220960 A1 | 9/2008 | Tsai |
| 2008/0233541 A1 | 9/2008 | Vreese et al. |
| 2008/0300469 A1 | 12/2008 | Kuo et al. |
| 2009/0082839 A1 | 3/2009 | Lindquist et al. |
| 2009/0210032 A1 | 8/2009 | Beiski et al. |
| 2009/0281433 A1 | 11/2009 | Saadat et al. |
| 2010/0152599 A1 | 6/2010 | DuHamel et al. |
| 2010/0204614 A1 | 8/2010 | Lindquist et al. |
| 2010/0204747 A1 | 8/2010 | Lindquist et al. |
| 2010/0255447 A1 | 10/2010 | Biris et al. |
| 2011/0168187 A1* | 7/2011 | Nelissen ................. A61F 5/566 |
| | | 128/848 |
| 2011/0171754 A1 | 7/2011 | Redmond et al. |
| 2011/0213216 A1 | 9/2011 | McKenna et al. |
| 2012/0172679 A1* | 7/2012 | Logan .................. A61B 5/6803 |
| | | 600/301 |
| 2012/0216820 A1 | 8/2012 | Scarberry et al. |
| 2013/0066236 A1 | 3/2013 | Herman et al. |
| 2013/0109932 A1 | 5/2013 | Saadat et al. |
| 2013/0116512 A1* | 5/2013 | Imran .................. A61B 5/6803 |
| | | 600/301 |
| 2013/0211270 A1 | 8/2013 | St. Laurent |
| 2013/0244339 A1 | 9/2013 | Ehrenkranz et al. |
| 2013/0253286 A1 | 9/2013 | Fridman |
| 2014/0114165 A1 | 4/2014 | Walker et al. |
| 2014/0135868 A1 | 5/2014 | Bashyam |
| 2014/0152464 A1* | 6/2014 | Smith ..................... A61F 5/566 |
| | | 340/870.02 |
| 2014/0190490 A1 | 7/2014 | Walker et al. |
| 2014/0230829 A1 | 8/2014 | Rogers |
| 2014/0323839 A1 | 10/2014 | McCreery |
| 2015/0057511 A1* | 2/2015 | Basu .................... A61B 5/6826 |
| | | 600/475 |
| 2015/0119759 A1 | 4/2015 | Gonzales |
| 2015/0190630 A1 | 7/2015 | Kent et al. |
| 2015/0217115 A1 | 8/2015 | Avitall |
| 2015/0355132 A1 | 12/2015 | Crooks et al. |
| 2016/0199215 A1 | 7/2016 | Kopelman |
| 2016/0240721 A1* | 8/2016 | Chu ....................... G01J 1/0407 |
| 2017/0135629 A1 | 5/2017 | Kent et al. |
| 2017/0143259 A1* | 5/2017 | Kent ..................... A61N 1/3601 |
| 2017/0156606 A1* | 6/2017 | Ferber .................. A61B 5/6824 |
| 2017/0196727 A1 | 7/2017 | Giridharagopalan |
| 2017/0290699 A1* | 10/2017 | Radmand .............. A61B 5/4557 |
| 2018/0000563 A1 | 1/2018 | Shanjani |
| 2018/0015282 A1 | 1/2018 | Waner et al. |
| 2018/0035932 A1 | 2/2018 | Massova |
| 2018/0035962 A1 | 2/2018 | Benndoref et al. |
| 2018/0116863 A1 | 5/2018 | Shah et al. |
| 2018/0177570 A1 | 6/2018 | Alauddin et al. |
| 2018/0317785 A1* | 11/2018 | MacDonald ........ A61B 5/02438 |
| 2019/0029587 A1 | 1/2019 | Walker et al. |
| 2019/0057700 A1 | 2/2019 | Kent et al. |
| 2019/0091061 A1 | 3/2019 | Radmand |
| 2019/0133730 A1 | 5/2019 | Adams et al. |
| 2019/0192259 A1 | 6/2019 | Kopelman et al. |
| 2019/0328574 A1 | 10/2019 | Flanagan |
| 2019/0343456 A1 | 11/2019 | Kahlert et al. |
| 2020/0029821 A1* | 1/2020 | Yoshida ................ A61B 5/0088 |
| 2020/0038231 A1 | 2/2020 | Radmand |
| 2020/0060611 A1 | 2/2020 | Radmand |
| 2020/0146630 A1* | 5/2020 | Joe ..................... A61B 5/02438 |
| 2020/0147473 A1 | 5/2020 | Maloney |
| 2020/0170574 A1 | 6/2020 | Radmand |
| 2020/0197655 A1 | 6/2020 | Shelly et al. |
| 2020/0229750 A1 | 7/2020 | Vanravenhorst-Bell et al. |
| 2020/0296454 A1 | 9/2020 | Shastry et al. |
| 2020/0375528 A1 | 12/2020 | Flanagan |
| 2021/0022913 A1 | 1/2021 | Damen |
| 2021/0113832 A1 | 4/2021 | Herron et al. |
| 2021/0321939 A1 | 10/2021 | Kent et al. |
| 2021/0330207 A1* | 10/2021 | Richards ............... A61B 5/0059 |
| 2021/0369203 A1* | 12/2021 | Bremer ................. A61B 5/0086 |
| 2022/0008243 A1 | 1/2022 | Osorio Martini et al. |
| 2022/0117777 A1 | 4/2022 | Lasry |
| 2022/0142571 A1* | 5/2022 | Dang .................. A61B 5/14539 |
| 2022/0257409 A1 | 8/2022 | Radmand |
| 2022/0304590 A1* | 9/2022 | Mathy .................. A61B 5/6823 |
| 2022/0330888 A1 | 10/2022 | Kim et al. |
| 2022/0346712 A1 | 11/2022 | Radmand |
| 2023/0329898 A1* | 10/2023 | Kruger .................... A61F 5/566 |

FOREIGN PATENT DOCUMENTS

| | | |
|---|---|---|
| CN | 104921833 A | 9/2015 |
| CN | 114641235 A | 6/2022 |
| EP | 3318216 B1 | 2/2020 |
| JP | 2018000930 A | 1/2018 |
| KR | 101645870 B1 | 8/2016 |
| KR | 20160095425 A | 8/2016 |
| KR | 20220043555 A | 4/2022 |
| SE | 3094281 | 12/2020 |
| WO | 2007106552 A2 | 9/2007 |
| WO | 2008048649 A2 | 4/2008 |
| WO | 2012027648 A2 | 3/2012 |
| WO | 2012027648 A3 | 8/2012 |
| WO | 2014107446 A1 | 7/2014 |
| WO | 2016087813 A1 | 6/2016 |
| WO | 2018115082 A1 | 6/2018 |
| WO | 2019185671 A1 | 10/2019 |
| WO | 2020193778 A1 | 10/2020 |
| WO | 2020245623 A1 | 12/2020 |

(56) References Cited

FOREIGN PATENT DOCUMENTS

| WO | 2021059284 A1 | 4/2021 |
|---|---|---|
| WO | 2021091583 A1 | 5/2021 |
| WO | 2021111132 A1 | 6/2021 |
| WO | 2021167855 A1 | 8/2021 |
| WO | 2022074627 A1 | 4/2022 |
| WO | 2022104354 A1 | 5/2022 |
| WO | 2022150539 A1 | 7/2022 |

OTHER PUBLICATIONS

U.S. Appl. No. 62/319,443, filed Apr. 7, 2016, Reza Radmand.

Takafumi Kato, Taihiko Yamaguchi, Kazuo Okura, Susumu Abe, Gilles J. Lavigne, Sleep less and bite more: Sleep disorders associated with occlusal loads during sleep, Journal of Prosthodontic Research, vol. 57, Issue 2, Apr. 2013, pp. 69-81, ISSN 1883-1958, https://doi.org/10.1016/j.jpor.2013.03.001.

Lee, S.-J.; Jeong, I.-D.; Kim, E.-8.; Park, J.-Y.; Jo, I.-H.; Han, J.-H.; Jung, T.-Y. s-Guard: Multisensor Embedded Obstructive Sleep Apnea and Bruxism Real-Time Data Transmission Intraoral Appliance Device. Appl. Sci.; May 4, 2021, 11, 4182. https://doi.org/10.3390/app11094182.

Jucevicius, M.; Ozi0nas, R.; Mazeika, M.; Marozas, V.; Jegelevicius, D. "Accelerometry-Enhanced Magnetic Sensor for Intra-Oral Continuous Jaw Motion Tracking". Sensors; Feb. 18, 2021, 21, 1409. https://doi.org/10.3390/s21041409.

Yeh, Kun-Ying, et al. "A Wirelessly Rechargeable Integrated System for Automatic Sleep Monitoring in a Smart Oral Appliance." International Journal of Automation and Smart Technology 7.2 (2017): 53-59.

Prosomnus Sleep Technologies "So . . . I Used This OAT Device Last Night . . . " PowerPoint Slide from 2022 MDSM Annual Meeting, May 13-15, 2022; 1 page.

Applied Thermoelectric Solutions, Introduction to Thermoelectrics and Medical Applications, Nov. 10, 2017, 33 pgs., https://thermoelectricsolutions.com/introduction-thermoelectrics-medical-applications/.

Arie Oliven, Treating Obstructive Sleep Apnea With Hypoglossal Nerve Stimulation, Medscape, Nov. 8, 2011, 9 pages, http://search.medscape.com/search/?q=Arie%200liven.

Bridgman et al., Mechanical Safety of Embedded Electronics for In-body Wearables: A Smart Mouthguard Study, dated Apr. 25, 2019, 36 pgs.

Castaneda, et al.; A review on wearable photoplethysmography sensors and their potential future application in health care; International Journal of Biosensors & Bioelectronics; dated Mar. 20, 2019; 19 pages.

European Patent Office; Rule 161 Communication for EP Application No. 20883753.4; dated Jun. 14, 2022; 3 pages.

European Patent Office; Rule 161 Communication for EP Application No. 21757720.4; dated Sep. 28, 2022; 3 pages.

European Respiratory Journal, Severity of obstructive sleep apnoea/hypopnoea syndrome and subsequent waking EEG spectral power, vol. 32, No. 3, Jun. 5, 2012, 6 pgs., https://erj.ersjournals.com/content/32/3/705.short.

Henderson et al, Near-infrared photonic energy penetration: can infrared phototherapy effectively reach the human brain?, Jan. 30, 2015, 18 pgs., https://www.dovepress.com/near-infrared-photonic-energy-penetration-can-infrared-phototherapy-ef-peer-reviewed-fulltext-article-NDT.

International Searching Authority, International Search Report and Written Opinion of PCT App. No. PCT/US20/16597, dated Apr. 27, 2020, 15 pgs.

International Searching Authority, Written Opinion of PCT Publication No. WO2014107466, Mar. 19, 2014, 4 pages.

International Searching Authority; International Preliminary Report on Patentability of the International Searching Authority for PCT/US20/16597; mailed on May 10, 2022; 10 pages.

International Searching Authority; International Preliminary Report on Patentability of the International Searching Authority for PCT/US21/18089; mailed on Aug. 23, 2022; 9 pages.

International Searching Authority; International Search Report and Written Opinion of the International Searching Authority for PCT/US2021/18089; mailed on Jun. 3, 2021; 16 pages.

International Searching Authority; International Search Report and Written Opinion of the International Searching Authority for PCT/US22/11536; mailed on May 5, 2022; 9 pages.

Kim et al., Biosens Bioelectron—Wearable salivary uric acid mouthguard biosensor with integrated wireless electronics, dated Aug. 1, 2015, 18 pgs.

Lissen Laboratories, Technology-Acostic Tooth Clip Sensor for Health, Jan. 23, 2020, 3 pgs., https://respiredx.com/index.php/technology /.

Lizette Borreli, Sleep Apnea May Increase Pneumonia Risk; CPAP May Increase Pulmonary Aspiration, Bacteria, Medical Daily, Mar. 3, 2014, 10 pages, http://www.medicaldaily.com/.

Marklund, Marie, et al., Oral Appliance Therapy in Patients With Daytime Sleepiness and Snoring or Mild to Moderate Sleep Apnea, A Randomized Clinical Trial, JAMA Intern Med, Aug. 2015, 15 pages.

Nabavi et al, A Smart Mandibular Advancement Device for Intraoral Cardiorespiratory Monitoring, Conference in Montreal Canada—Jul. 20-24, 2020, 6 pgs. https://ieeexplore.ieee.org/document/9176520.

National Institute of Health Public Access Author Manuscript, EEG Recording and Analysis for Sleep Research, Oct. 2009, 21 pgs., https://www.ncbi.nlm.nih.gov/pmc/articles/PMC2824445/.

Norman Wolkove, et al., Long-term compliance with continuous positive airway pressure in patients with obstructive sleep apnea, Oct. 2008, 8 pages, www.ncbi.nlm.nih.gov/.

Nyxoah, Enjoy the comfort of Restful Nights, What is OSA?, Aug. 27, 2016, 3 pages, http://www.nyxoah.com/patients/what-is-osa.

Nyxoah, Sleep Apnea, Nyxoah, 2015, 5 pages, http://www.nyxoah.com/sleep-apnea.

Opel et al., Light-emitting Diodes—A Brief Review and Clinical Experience, The Journal of Clinical Aesthetic Dermatology, Jun. 2015, vol. 8, Nov. 6, 9 pgs.

ResearchGate, Sublingual electrical stimulation of the tongue during wakefulness and sleep, Sep. 2001, 1 page, https://www.researchgate.net/publication/11839659.

Seshadri et al; Wearable Sensors for Covid-19: A Call to Action to Harness Our Digital Infrastructure for Remote Patient Monitoring and Virtual Assessments; Frontiers in Digital Health, vol. 2; Jun. 23, 2020; 11 page.

Shimada et al., Evaluation of a new reflectance pulse oximeter for clinical applications, Sep. 1991, 1 pg., https://pubmed.ncbi.nlm.nih.gov/1817222/.

Silva et al., Development and Implementation of an Intraoral Device for Occlusal Stability during Sports Performance: A Case Report, dated Nov. 8, 2018, 28 pgs.

Sporttechie, Pilot Program Has Select NFL Teams Wearing Sensor-Laden Mouth Guards to Study Concussions, Aug. 28, 2019, 3 pgs., https://www.sporttechie.com/nfl-mouth-guard-sensors-concussion-technology.

TEC Microsystems, Miniature Thermoelectric Generators, Aug. 14, 2020, 5 pgs., https://www.tec-microsystems.com/products/thermoelectric-generators/index.html.

Tekscan, Inc., Measure Force with FlexiForce Force Sensors, 8 pages, Apr. 12, 2015, https://www.tekscan.com/product-group/embedded-sensing/force-sensors.

True Wearables, Oxxiom—Expand Your Limits Control What You Can Measure Aim Higher, 2015, 5 pgs., https://www.truewearables.com/.

United States Patent and Trademark Office, Non-Final Office Action of U.S. Appl. No. 16/152,778, dated Sep. 14, 2020, 9 pages.

United States Patent and Trademark Office, Office Action of U.S. Appl. No. 16/781,417, dated Apr. 16, 2020, 14 pgs.

United States Patent and Trademark Office; Advisory Action Before the Filing of an Appeal Brief for U.S. Appl. No. 16/781,417; dated Feb. 3, 2021; 3 pages.

(56) References Cited

OTHER PUBLICATIONS

United States Patent and Trademark Office; Final Office Action for U.S. Appl. No. 16/781,417; dated Nov. 17, 2020; 17 pages.
United States Patent and Trademark Office; Final Office Action for U.S. Appl. No. 16/781,417; dated Feb. 9, 2022; 20 pages.
United States Patent and Trademark Office; Final Office Action for U.S. Appl. No. 17/854,357; dated Jan. 25, 2023; 16 pages.
United States Patent and Trademark Office; Non-Final Office Action for U.S. Appl. No. 16/781,417; dated Jul. 14, 2021; 15 pages.
United States Patent and Trademark Office; Non-Final Office Action for U.S. Appl. No. 17/175,731; dated Apr. 7, 2021; 17 pages.
United States Patent and Trademark Office; Non-Final Office Action for U.S. Appl. No. 17/854,357; dated Oct. 4, 2022; 15 pages.
United States Patent and Trademark Office; Notice of Allowance for U.S. Appl. No. 16/202,204; dated Mar. 15, 2021; 10 pages.
United States Patent and Trademark Office; Notice of Allowance for U.S. Appl. No. 16/593,046; dated Sep. 28, 2021; 9 pages.
United States Patent and Trademark Office; Notice of Allowance for U.S. Appl. No. 16/673,077; dated Dec. 3, 2021; 12 pages.
United States Patent and Trademark Office; Notice of Allowance for U.S. Appl. No. 16/781,417; dated May 11, 2022; 10 pages.
United States Patent and Trademark Office; Notice of Allowance for U.S. Appl. No. 17/175,731; dated Apr. 26, 2021; 8 pages.
Vatansever et al., Far infrared radiation (FIR): Its biological effects and medical applications, Photon Lasers Med 2012; 12 pgs.
Very Well Health, Electronic Tongue Device for Sleep Apnea, dated Apr. 29, 2019, 4 pgs., https://www.verywellhealth.com/hypoglossal-nerve-stimulator-for-treating-sleep-apnea-3015195.
Wax et al., A Comparison of Transmittance and Reflectance Pulse Oximetry During Vascular Surgery, International Anesthesia Research Society, Dec. 2009, 3 pgs.
Wikipedia, Pulse Oximetry, Wikipedia, Oct. 1, 2004, 9 pages, https://en.wikipedia.org/wiki/Pulse_oximetry.
FDA: Pulse Oximeter Accuracy and Limitations: FDA Safety Communication; Nov. 16, 2023; 5 pages. https://www.fda.gov/medical-devices/safety-communications/pulse-oximeter-accuracy-and-limitations-fda-safety-communication.
Niwayama, et al. "Tissue Oximeter with Selectable Measurement Depth Using Spatially Resolved Near-Infrared Spectroscopy", Sensors 2021, 21, 5573. https://doi.org/10.3390/s21165573; 11 pages. https://www.ncbi.nlm.nih.gov/pmc/articles/PMC8402253/pdf/sensors-21-05573.pdf.
International Searching Authority; International Search Report and Written Opinion issued for PCT/US2024/021971 on Jun. 26, 2024; 14 page.
Japan Patent Office; Office Action issued for JP 2022-535827; dated Oct. 17, 2024; 6 pages.

\* cited by examiner

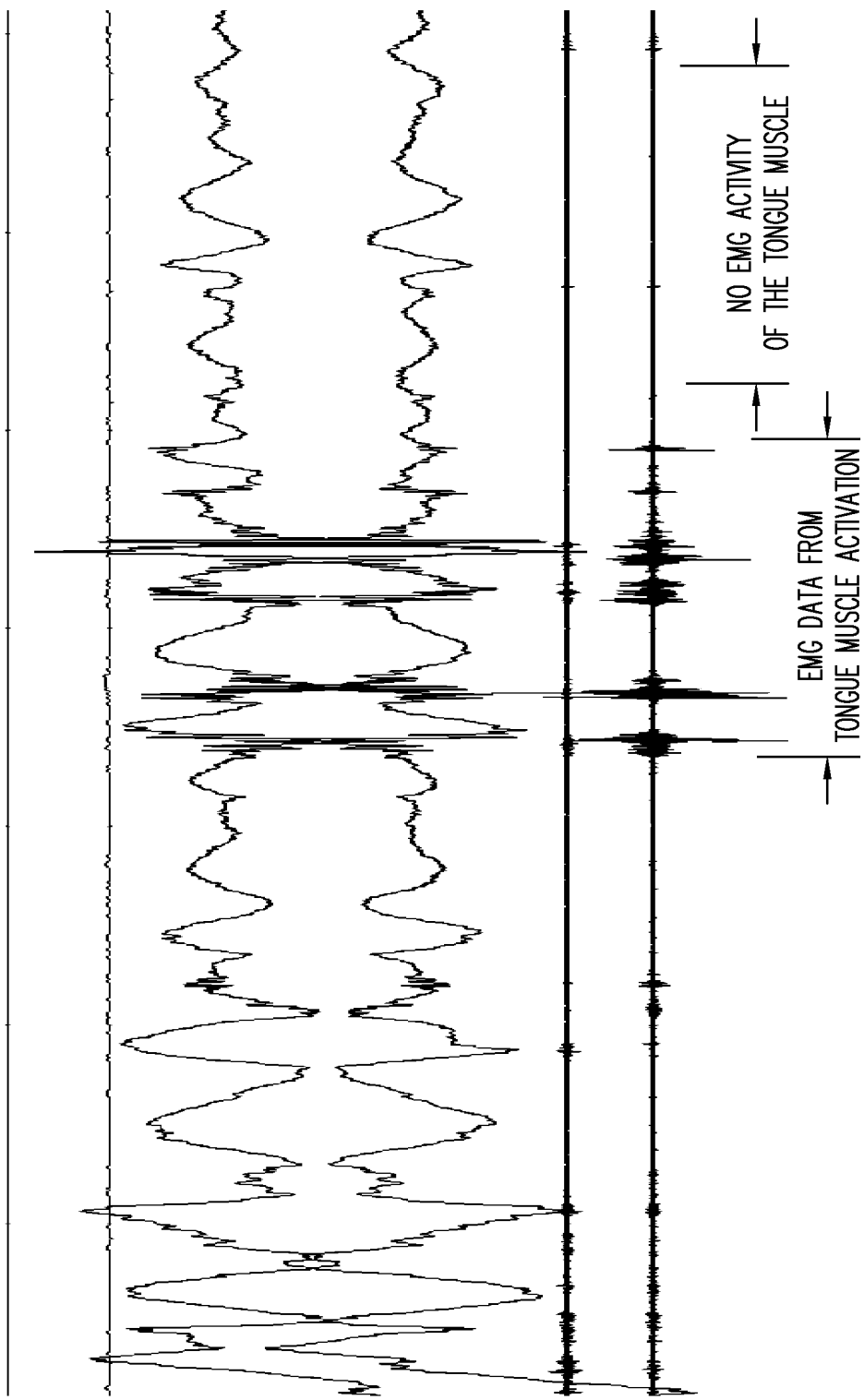

ORAL APPLIANCE FOR THE TREATMENT OF SLEEP APNEA

CROSS-REFERENCE TO RELATED APPLICATIONS

This application is a continuation-in-part of and claims priority to U.S. patent application Ser. No. 18/209,298 filed Jun. 13, 2023. This application claims the benefit of and priority to U.S. Provisional Patent Application No. 63/497,605 filed on Apr. 21, 2023, the entire contents of each of which is incorporated by reference herein.

BACKGROUND

Sleep apnea is a common medical condition during which a person experiences one or more pauses in breathing, and in some instances, experiences shallow breaths during sleep. While there are several types of sleep apnea, the most common type is obstructive sleep apnea. In this medical condition, one or more of the person's throat muscles relax during sleep causing surrounding tissues in the posterior portions of the mouth, nose and throat to collapse, thereby creating a pharyngeal obstruction that can block the upper airway. Persons suffering from obstructive sleep apnea have inadequate oxygen exchange during sleep, which can lead to daytime fatigue, lack of concentration and mood changes. Left untreated, obstructive sleep apnea can have a significant impact on a person's health, often leading to cardiovascular, stroke and metabolic disorders.

To reduce this risk, various nonsurgical approaches have been employed. One such nonsurgical approach includes using standardized oral appliances to incrementally advance and/or protrude the mandible (lower jaw) relative to the maxilla (upper jaw). These standardized oral appliances, commonly referred to as a mandibular advancement device, ("MAD"), typically include upper and lower dental trays, whereby the lower dental tray is designed to advance the mandible, and hence, move the tongue forward to increase the space in the posterior part of the throat and the oropharynx, which in turn may serve to increase the flow of air during sleep. The distance (degree of advancement) required to protrude and/or reposition the mandible may be, at least in part, dependent on the severity of the individual's obstructive sleep apnea, as well as psychological variables among the users. A disadvantage of using these standard oral appliances is that they may not sufficiently provide for and/or address individualized anatomical variances, such as difference in dental arches, dentition alignment and/or jaw flexibility. Another disadvantage is that in instances where the degree of advancement is excessive, the appliance may lead to long-term temporomandibular joint ("TMJ") disorders, muscular aggravation, dentition discomfort and/or myofascial disorders. As a result, use of these standard appliances has an approximate compliance rate of 75% over a 2-year period. For a detailed study of compliance with use of MAD, see *Non-CPAP therapies in obstructive sleep apnoea: mandibular advancement device therapy*, see Eur Respir J 2012; 39:1241-1247, which is incorporated by reference in its entirety. Thus, such oral appliances may not treat obstructive sleep apnea in a manner that prevents and/or limits impacts on a person's health.

In view of the disadvantages associated with currently available methods and devices for treating obstructive sleep apnea, there is a need for a device and method that treats obstructive sleep apnea while storing patient behavior and/or medical data relating to a user's oxygen saturation, breathing pattern, snoring pattern and/or clenching/grinding behaviors, that can assist medical providers in the design, improvement and/or modification of specialized treatment measures for individual patients. Further, there is a need for a device and method that treats obstructive sleep apnea in a single removable oral appliance and prevents and/or limits long-term TMJ disorders, muscular aggravation and/or myofascial disorders that may occur with continued use of currently available appliances.

BRIEF DESCRIPTION

According to an aspect of this disclosure, an exemplary embodiment of an oral appliance may include a mouthpiece that is configured to be positioned in an oral cavity of a user. The mouthpiece may include an anterior wall configured to cover facial surfaces of the user's dentition, a posterior wall configured to cover lingual surfaces of the user's dentition, and a transverse wall extending between the anterior wall and the posterior wall. An electronic assembly may be coupled to the mouthpiece and the electronic assembly may include an oxygen sensor coupled to the anterior wall and configured to be oriented toward soft tissue of the user's mouth to determine an oxygen saturation level of the user.

According to an aspect of this disclosure, an exemplary embodiment of an oral appliance may include a mouthpiece configured to be positioned in an oral cavity of a user. The mouthpiece may include an anterior wall configured to cover facial surfaces of the user's dentition, a posterior wall configured to cover lingual surfaces of the user's dentition, and a transverse wall extending between the anterior wall and the posterior wall. An electronic assembly may be coupled to the mouthpiece. The electronic assembly may include an oxygen sensor coupled to the anterior wall and configured to be oriented toward soft tissue of the user's mouth to determine an oxygen saturation level of the user and collect oxygen saturation (SpO2) and photoplethysmography (PPG) data.

According to an aspect of this disclosure, an exemplary embodiment of a oral appliance may include a mouthpiece configured to be positioned in an oral cavity of a user. The mouthpiece may include an anterior wall configured to cover facial surfaces of the user's dentition, a posterior wall configured to cover lingual surfaces of the user's dentition, and a transverse wall extending between the anterior wall and the posterior wall. An appendage may extend away from the anterior wall in a direction towards soft tissue of the user's mouth and define a space within the appendage. An electronic assembly including an oxygen sensor and may be positioned at least partially within the space within the appendage, and the appendage and electronic assembly may together be configured for orienting the oxygen sensor toward the soft tissue of the user's mouth.

BRIEF DESCRIPTION OF THE FIGURES

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which:

FIG. 33 is a chart illustrating the difference between electromyogram data from tongue muscle activation versus electromyogram data in the absence of tongue muscle activation.

Figure 1:
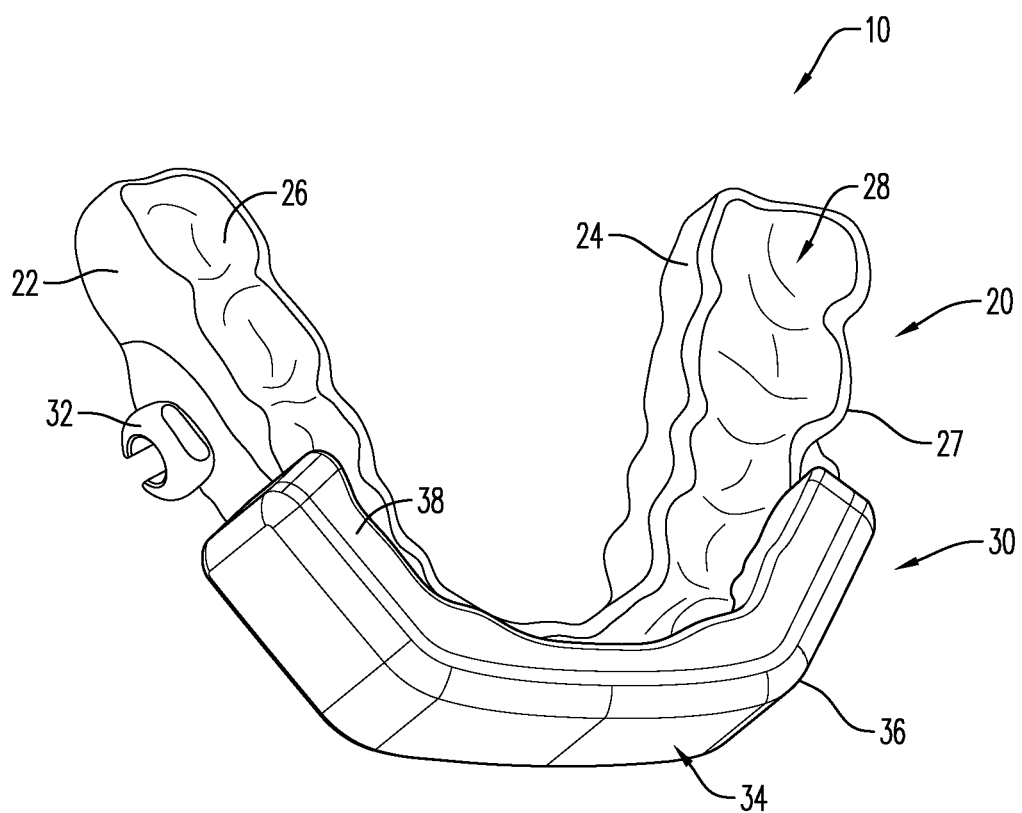
FIG. 1 is a perspective view of an exemplary oral appliance in accordance with aspects of the present disclosure.
Figure 2:
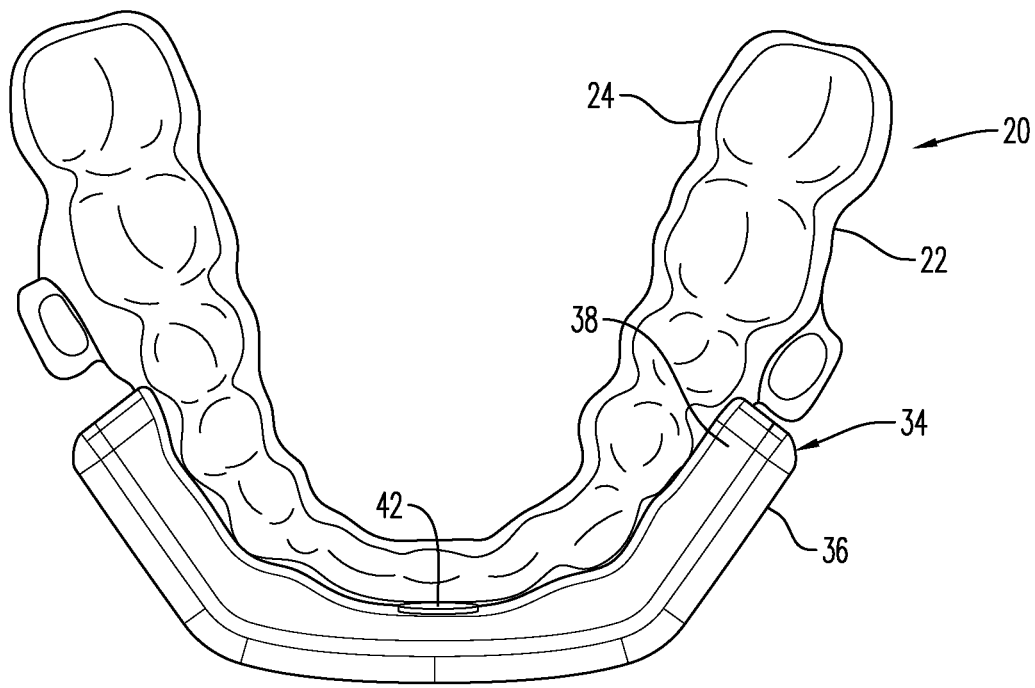
FIG. 2 is a plan view of the oral appliance of FIG. 1

Various features, aspects, and advantages of the embodiments will become more apparent from the following detailed description, along with the accompanying figures in which like numerals represent like components throughout the figures and text. The various described features are not necessarily drawn to scale but are drawn to emphasize specific features relevant to some embodiments.

DETAILED DESCRIPTION

Reference will now be made in detail to various embodiments. Each example is provided by way of explanation and is not meant as a limitation and does not constitute a definition of all possible embodiments.

For purposes of illustrating features of the embodiments, embodiments will now be introduced and referenced throughout the disclosure. Those skilled in the art will recognize that this example is illustrative and not limiting and is provided purely for explanatory purposes.

As used herein, "coupled" may refer to any manner of assembling or connecting two components together in any suitable manner, such as, by way of example only: attaching directly or indirectly (e.g., attached to a surface), disposing on, disposing within, disposing substantially within, formed with, embedding within, embedded substantially within, etc. "Coupled" may further include fixedly attaching two components (such as by using a screw or embedding a first component into a second component during a manufacturing process), but does not so require. That is, two components may be coupled temporarily simply by being in physical contact with one another.

In an embodiment, and with particular reference to FIGS. 1-6, an oral appliance 10 for treatment of sleep apnea in a user is provided. The oral appliance 10 generally includes a mouthpiece 20 and a housing assembly 30 coupled to the mouthpiece 20. In an embodiment, the mouthpiece 20 is "customizable," that is, customized to the individual user's mouth in such a manner that it provides for a comfortable fit over and around surfaces of the user's hard (teeth/dentition) and/or soft tissues (general mouth structure, including gingiva). When customized, the mouthpiece 20 may fit over temporary, permanent, primary natural and/or artificial lower or upper dentition of adult and/or child users. The mouthpiece 20 may be configured to receive a removable denture of the user. According to an aspect, the mouthpiece 20 is fabricated over the upper jaw or lower jaw with partial or complete absence of dentition. When customized, the mouthpiece 20 can be formed of any suitable self-conforming material that may be adaptable to variances and/or changes in mouth structure, or through use of a dental impression of the individual user's dentition, as would be understood by a person having ordinary skill in the art. In other words, a mandibular impression and/or a dental impression can be taken, whereby a negative imprint of the user's hard and/or soft tissues are used to create a positive reproduction (or cast) customized for the user. In aspects, the mandibular impression and/or dental impression may be a digital dental impression taken with 3D scanning technology or other suitable technologies.

The types of materials selected to form the mouthpiece 20 would be known to one of ordinary skill in the art and includes polymers, thermoplastics, acrylics, silicone, rubber, metal wires or any other material that can be used to form the mouthpiece 20 conformed to the user's dentition. In an embodiment, the materials are medical-grade, latex-free, BPA-free and any other material known to minimize patient health risks. According to an aspect, the mouthpiece 20 may be formed from the impression made in a suitable impression material, such as, for example, alginate, polysulfide, polyvinyl siloxane, silicone, or the like. The mouthpiece material may also be selected, particularly from polymers, for its ability to have a pharmaceutical compound incorporated within the structural matrix.

The mouthpiece 20 includes an anterior wall 22 configured to cover facial surfaces of a user's dentition, a posterior wall 24 configured to cover lingual surfaces of the user's dentition, and a transverse wall 26 interconnecting the anterior wall 22 and the posterior wall 24 and configured to cover an occlusal surface of the user's dentition. The mouthpiece 20 defines a central channel 28 bounded by the anterior wall 22, the posterior wall 24, and the transverse wall 26. The central channel 28 is configured to be positioned over one or more of the user's dentition such that the mouthpiece 20 is secured thereon. When the mouthpiece 20 is in use, the central channel 28 may receive the user's dentition and may extend over and/or cover occlusal or bite surfaces of the user's dentition. The posterior wall 24 of the mouthpiece 20 extends between the user's dentition and the user's tongue. In an embodiment, the anterior wall 22 of the mouthpiece 20 is configured to extend between the user's dentition and the user's cheek.

The mouthpiece 20 may include a socket 32 coupled to the anterior wall 22 of the mouthpiece 20. The socket 32 is configured to couple to a strut assembly, such as, for example, one or more of the strut assemblies disclosed in U.S. patent application Ser. No. 17/737,470 filed May 5, 2022, the entire contents of which are incorporated by reference herein. The oral appliance 10, in combination with the strut assemblies, may be configured to position the bottom jaw of a user in a direction that is forward from the natural position of the user's jaw to aid in the treatment of sleep apnea in the user. The best jaw position for the user may be determined by a dentist and prescribed to a lab that is tasked with fabricating the oral appliance 10.

The housing assembly 30 of the oral appliance 10 generally includes a housing 34 and a printed circuit board assembly 40 (FIGS. 2 and 3) positioned within the housing 34. The housing 34 has an anterior portion 36, and a posterior portion 38 coupled to the anterior wall 22 of the mouthpiece 20. The anterior portion 36 and the posterior portion 38 may be monolithically formed with one another to form the housing 34, and in other aspects the anterior portion 36 and the posterior portion 38 may be separate components that are otherwise attached to one another. The posterior portion 38 of the housing 34 conforms to and is coupled to the anterior wall 22 of the mouthpiece 20 using any suitable fastening engagement, such as, for example, adhesives, fasteners, heat treatment, or the like. In other aspects, the posterior portion 38 of the housing 34 may be monolithically formed with the mouthpiece 20.

Figure 3:
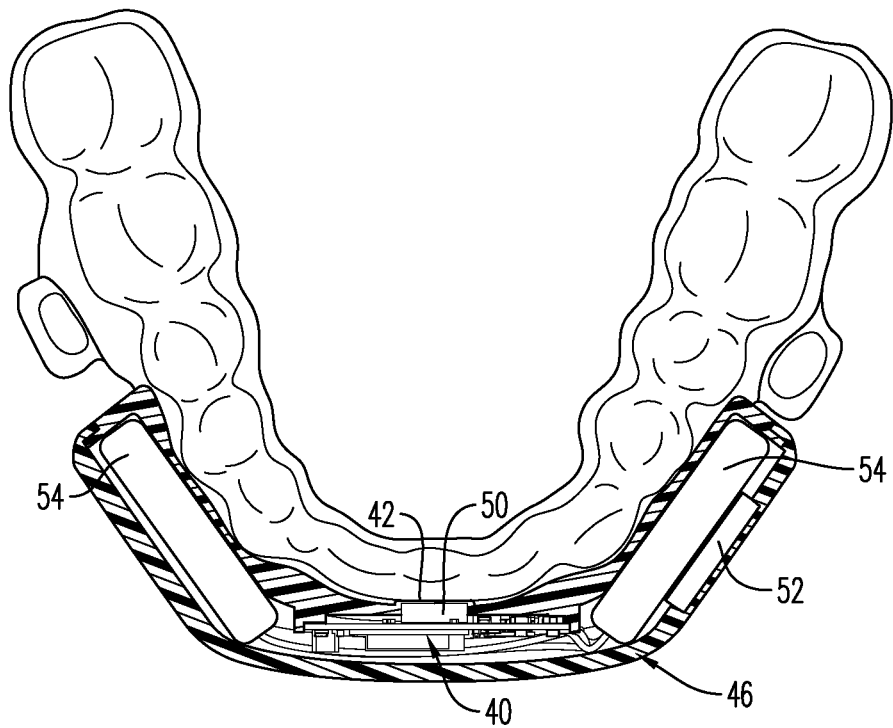
FIG. 3 is a plan view of the oral appliance of FIG. 1, with a cross-section taken along a horizontal plane of a housing assembly of the oral appliance.
Figure 4:
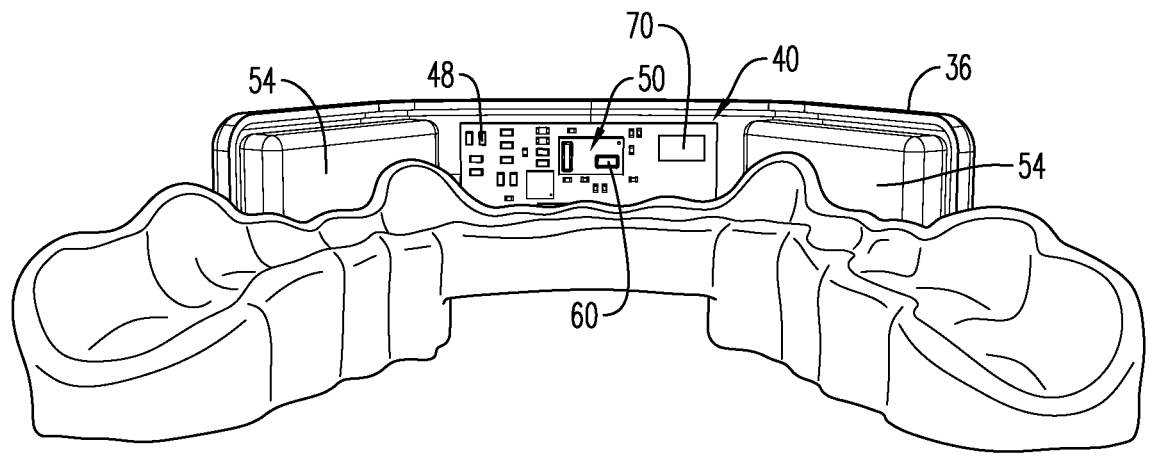
FIG. 4 is a posterior view, with a posterior housing half removed, illustrating internal electrical components of a housing assembly of the oral appliance of FIG. 1.
Figure 5:
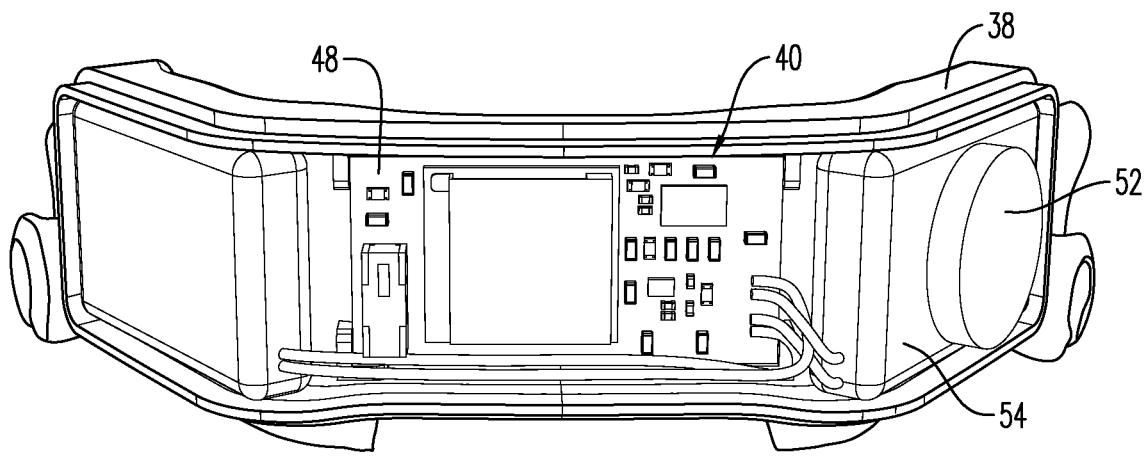
FIG. 5 is an anterior view, with an anterior housing half removed, illustrating the internal electronic components of the housing assembly of FIG. 4.
Figure 6:
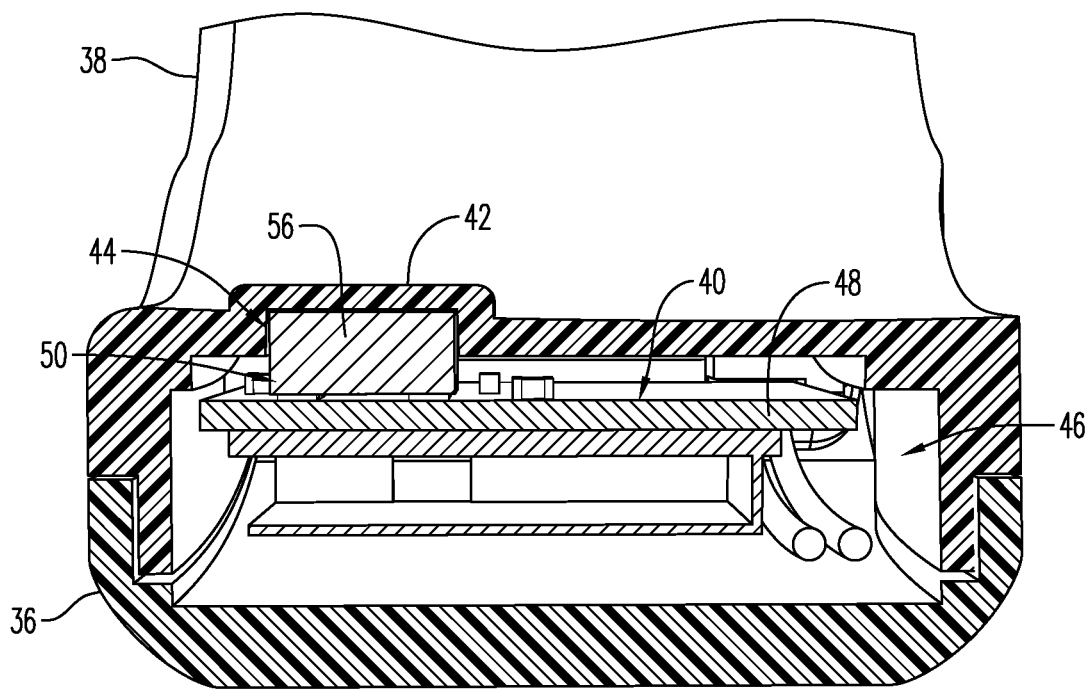
FIG. 6 is a side, cutaway view of the housing assembly of the oral appliance of FIG. 1.

The posterior portion 38 protrudes anteriorly away from the mouthpiece 20 and perpendicularly away from a gingival edge 27 of the mouthpiece 20. The posterior portion 38 may be fabricated from a light-transmissive material, such as, for example, polycarbonate, acrylic, polyethylene terephthalate, amorphous copolyester (modified forms of polyester, such as combinations of diacids and diols), polyvinyl chloride, liquid silicone rubber, polyethylene, styrene methyl methacrylate, or the like. In aspects and as illustrated in FIG. 3, only a portion of the posterior portion 38 may be light-transmissive, such as, for example, an optical window 42 that is positioned at a midline of the posterior portion 38. With reference to FIG. 6, the optical window 42 is monolithically formed with the posterior portion 38 and may also protrude posteriorly from the posterior portion 38 to define a recess 44 therein for receiving an optical assembly 50 therein, as will be described in more detail below. As shown herein, the material forming the posterior portion 38 differs from the material forming the anterior portion 36.

Figure 8A:
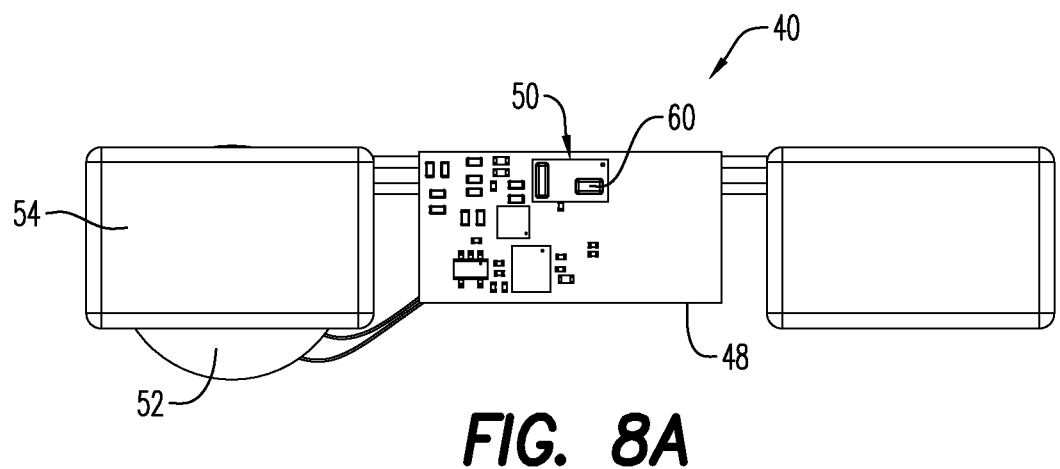
FIG. 8A is an anterior view of the internal electronic components of FIG. 6.
Figure 8B:
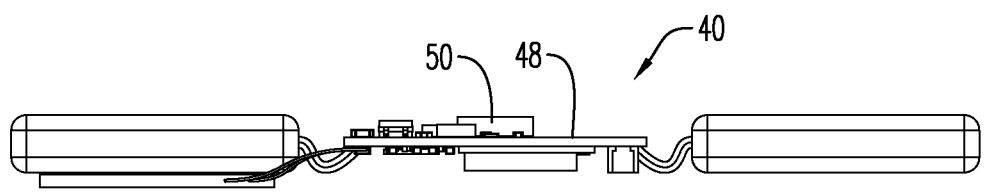
FIG. 8B is a top view of the internal electronic components.
Figure 8C:
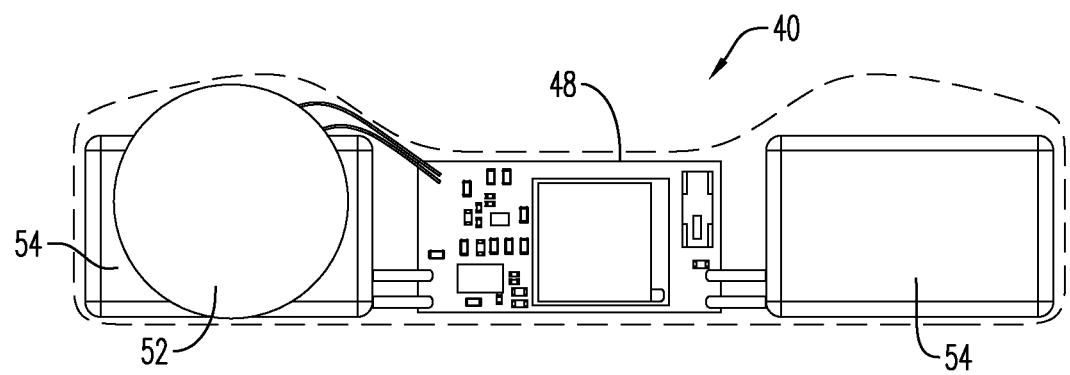
FIG. 8C is a posterior view of the internal electronic components.

With particular reference to FIGS. 8A-C, the housing 34 defines an inner chamber 46 therein that extends along a length of the housing 34 for housing the printed circuit board assembly 40 therein. The printed circuit board assembly 40 includes a printed circuit board 48, the optical assembly 50, and in some aspects, a microprocessor (not labeled) and other suitable electronic components. For example, the printed circuit board assembly 40 may further include a wireless power charging coil 52 positioned at a first end portion of the printed circuit board 48 and one or more batteries 54, such as, for example, a lithium-polymer battery (LiPo) rechargeable batteries, positioned at the first end portion and a second end portion of the printed circuit board 48.

The optical assembly 50 is positioned adjacent the optical window 42 of the housing 34 and includes an optical housing 56 supported on a posterior side of the printed circuit board 48 and an oxygen sensor 60 supported in the optical housing 56 and electrically coupled to the microprocessor of the printed circuit board 48. In aspects, the optical assembly 50 may be supported in the recess 44 (FIG. 6) defined by the optical window 42 such that the optical assembly 50 is oriented on a sagittal plane of the user's oral cavity and towards buccal gingiva of the user when the oral appliance 10 is worn by the user.

Figure 7:
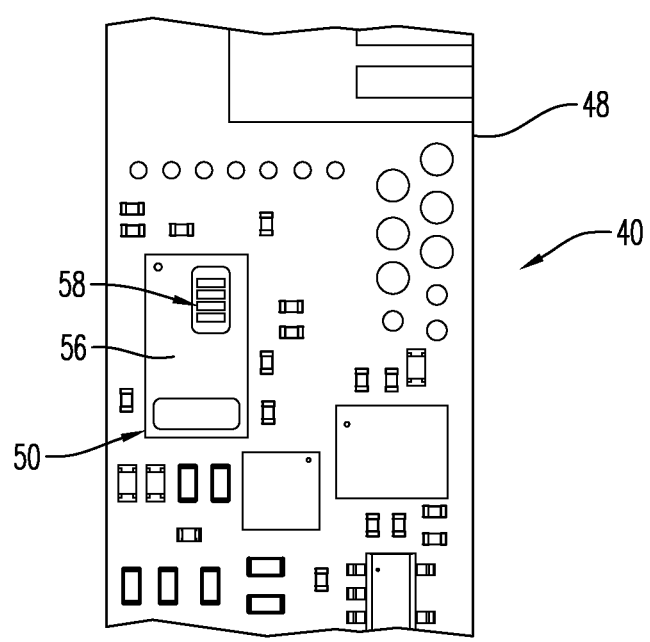
FIG. 7 is a plan view illustrating the internal electronic components of FIG. 6.
Figure 9:
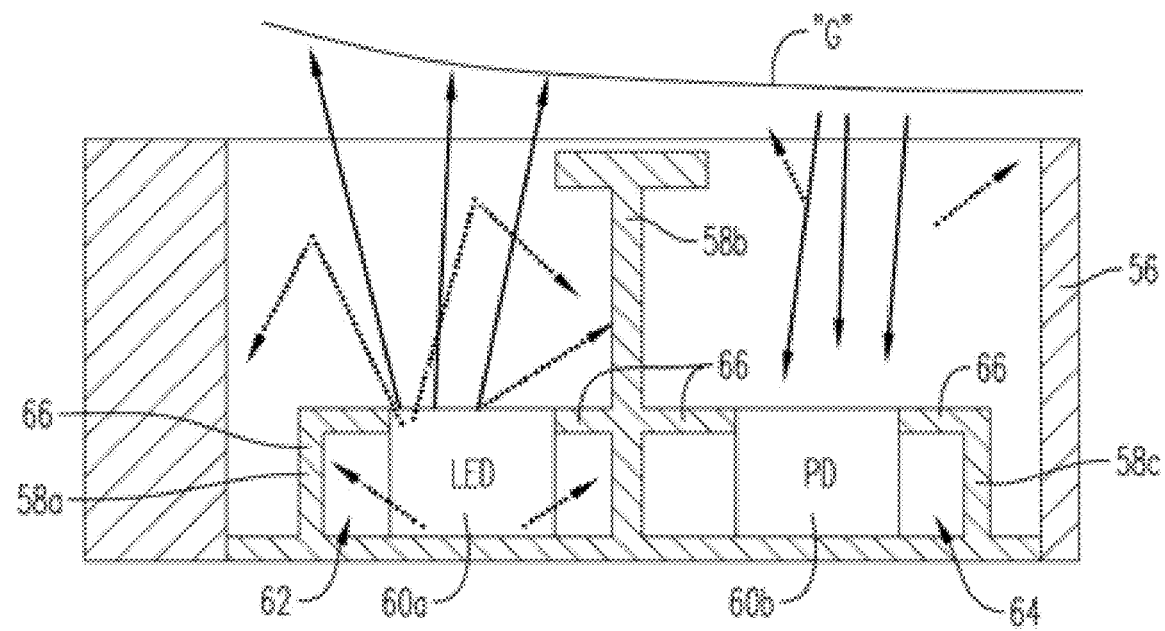
FIG. 9 is a schematic illustration of components of an oxygen sensor positioned between isolation barriers of the oral appliance of FIG. 1.

With reference to FIGS. 7 and 9, the optical housing 56 may include a plurality of isolation baffles or barriers 58 coupled to the printed circuit board 48. The barriers 58 are arranged in parallel relation with one another. Adjacent barriers, such as, for example, barriers 58a, 58b, define a first space 62 therebetween in which one or more components of the oxygen sensor 60 are positioned. The oxygen sensor 60 may be a reflectance pulse oximeter configured to monitor/sense the oxygen saturation of a user by analyzing the change in color of the user's blood. The reflectance pulse oximeter 60 may measure the pulse rate of the user, typically in beats per minute, based on variations and/or deviations in the user's oxygen saturation. An exemplary pulse oximeter may use light-based technology to sense the actual oxygen saturation of hemoglobin of the user. According to an aspect, the pulse oximeter 60 includes light emitting diodes (LEDs) 60a and photodiodes (PD) 60b. The LED 60a is configured to transmit red and infrared lights to vascular surfaces of the user's gingiva "G" and the photodiodes 60b receive the light reflected from the gingiva "G" to determine changes in oxygen level in the user's gingiva "G" (e.g., the alveolar mucosa). In an aspect, the transmitted light may include blue light or green light, or a combination of lights according to the exemplary embodiments or otherwise consistent with this disclosure.

The barriers 58 provide optical isolation between the LED 60a and the detection photodiode 60b to improve a signal-to noise ratio through tissue. For example, as shown in FIG. 9, the LED 60a may be received in the first space 62 between adjacent barriers 58a, 58b, and the photodiode 60b may be received in a second space 64 defined between adjacent barriers 58b, 58c. Each of the isolation barriers 58 may include a horizontal wall 66 extending perpendicularly therefrom to prevent laterally-projecting light from escaping the spaces 62, 64 between the barriers 58. In this way, the barriers 58 are configured to isolate the light projecting from the LEDs 60a. Moreover, the optical reflections reject both dc and ac ambient light interference while directly improving signal quality and effectively reducing errors in physiological data acquisition. The spacing between the LEDs 60a and the photodiodes 60b is optimized to reduce backscatter from "blood-less" tissues and the barriers 58 reduce LED 60a to photodiode 60b crosstalk.

Current commercial FDA cleared pulse oximeter devices are used, for example, to measure a body's oxygen saturation by using optical modules. These devices are typically used externally on the skin surface and measure oxygen saturation via transmissive or reflectance technique(s) using one LED and one photo diode. According to the FDA, $SpO_2$ readings obtained by these devices should be considered an estimate of arterial oxygen saturation. For example, commercial medical grade oximeters may record oxygen saturation values which are between about 4% and about 6% of the actual arterial blood oxygen readings. For example, if an FDA-cleared pulse oximeter reads 90%, then the true oxygen saturation in the blood is generally between 86-94% or possibly 84-96%.

Oral mucosa in particular comprises a different tissue histology than skin, therefore the optical module design of existing commercial pulse oximeter devices is not necessarily optimal for intra-oral oxygen saturation data collection. At least one possible reason an existing commercial pulse oximeter device may not be optimal for intra-oral use is the number of LEDs and PDs as well as their positions relative to one another. In intra-oral applications, the light intensity and the angle of reflection of the light against the tissue may cause saturation (too much light intensity) or scattering of the light. Oral mucosa requires less depth penetration for the light and is prone to having excessive light scattering of the glossy mucosa layer, secondary to the high moisture content of the intra-oral tissue. The epithelial thickness of the oral mucosa is roughly between 0.3 mm-0.5 mm whereas the epithelial thickness of the skin, i.e., fingertip is between about 1 mm-3 mm.

Figure 9A:
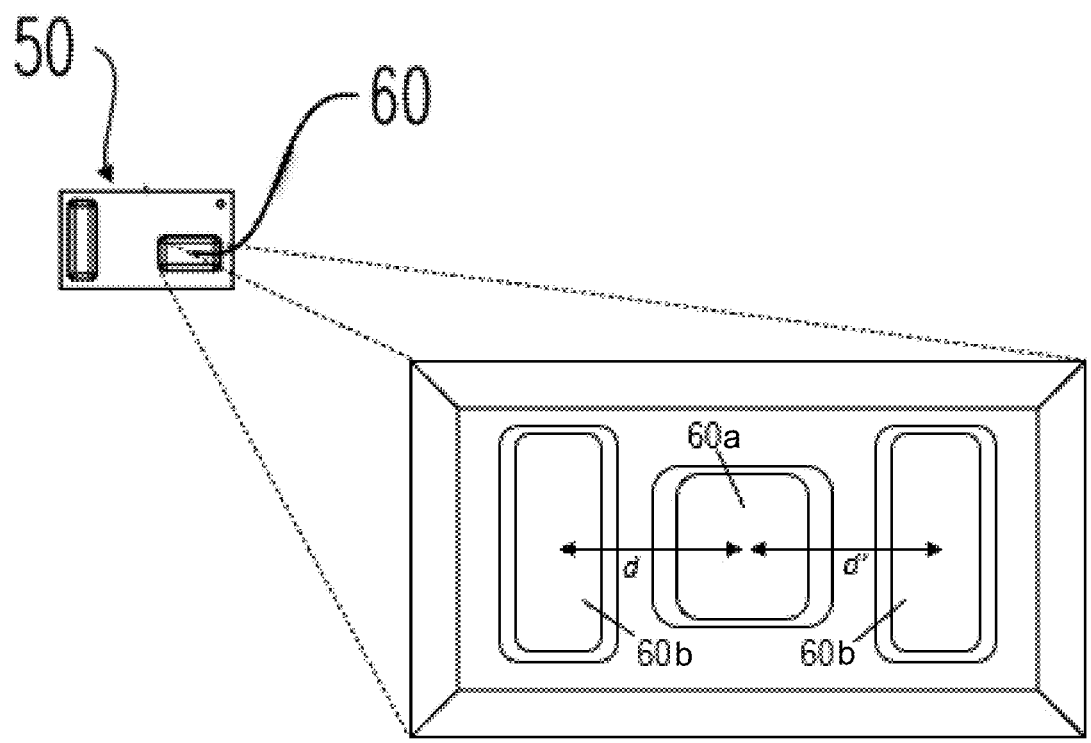
FIG. 9A is an oxygen sensor according to an exemplary embodiment.

FIG. 9A shows an exemplary embodiment of an intra-oral oxygen sensor configured for minimizing the effect of light scatter from the oral mucosa according to this disclosure. The oxygen sensor 60 according to the exemplary embodiment is positioned on optical assembly 50 and includes without limitation an LED 60a and two or more PDs 60b. The oxygen sensor 60 is dimensioned and designed to position the two PDs 60b on opposite sides of the LED 60a at respective distances d, d' (for example, centerline to centerline) from the LED 60a. In an exemplary configuration, each of the distances d, d' is in the range of approximately 3 mm to approximately 5 mm for optimal intra-oral measurement depths up to approximately 2 mm. The exemplary configuration has been found to result in a higher yield in PPG wave quality with less scattering. This effect may be due at least in part to the fact that the oral mucosa is thinner than the skin of the finger and less depth is needed to reach the vascular complexes at which the measurements will be performed within the oral tissue. The exemplary embodiment and configuration shown and described with respect to FIG. 9A has also been found to enhance the quality of the physiological data collection with lower LED power consumption, since the mucosal thickness does not require a deeper light penetration. The exemplary configuration has also been found to increase the speed at which the sensor reacts to changes in blood oxygen levels.

In other configurations the distances d, d' may be varied and different configurations have been found to have optimal sensitivity within particular depth ranges. For example, distances within a range of about 6 mm to 8 mm had peak sensitivity at about 2 mm depth, distances within about 9 mm to about 14 mm had peak sensitivity at about 3 mm to 4 mm depth, and distances on the order of about 20 mm to about 30 mm had peak sensitivity at about 5 mm to about 6 mm depth.

In an aspect and without limitation, a biocompatible adhesive or cohesive material may be applied to coat and hermetically seal over the optical components (e.g., LEDs/PDs) in any of the exemplary embodiments according to this disclosure or embodiments consistent with this disclosure. The biocompatible adhesive or cohesive material may have a low refraction index. In another aspect, the biocompatible adhesive or cohesive material may be less than about 1 mm thick. The biocompatible adhesive or cohesive material may be used in addition to or in substitution to the optical housing 56.

In aspects, the oral appliance 10 may further include one or more of the following additional components: a pressure sensor (not labeled), an airflow sensor (not labeled), a noise detector (not labeled), an actigraphy sensor (not labeled), a stimulator (not labeled), and an electroencephalogram (EEG) sensor 70 (FIG. 4) configured to differentiate various EEG rhythms and to determine, based on these detected rhythms, the various consciousness and sleep states of the user. It is contemplated that the oral appliance 10 may be able to assist with the diagnosis of brain related health conditions, such as epilepsy, by way of recording the user's brain activity-such brain activity may be collected by a data recorder (not labeled) for review and analysis. For further details regarding the EEG sensor 70, reference may be made to U.S. patent application Ser. No. 16/781,417 filed Feb. 4, 2020 (now U.S. Pat. No. 11,375,951), the entire contents of which are incorporated by reference herein. The EEG sensor 70 may be positioned at a portion of the mouthpiece 20 that is adjacent a buccal side of a maxillary bone of the user when the oral appliance is worn. That is, the EEG sensor may be located over the alveolar mucosa between the upper gums and inner lip/cheek of the user.

According to an aspect, the oral appliance 10 may include a transceiver (not labeled). The transceiver may be configured to remotely monitor any additional components provided on and/or within the mouthpiece 20. In an embodiment, the transceiver may be configured for use with a customized web-based application for a handheld wireless communication device. The customized web-based application may include features such as, a graph of the user's sleep position and chart and/or graphical data related to oxygen saturations of hemoglobin and the pressure applied to occlusal surfaces of the user's dentition. According to an aspect, the customized web-based application may include data related to the user's heart rate. In an embodiment, the transceiver communicates with handheld wireless communication devices having Bluetooth® capabilities. The transceiver may be communicable with handheld wireless communication devices, such as, for example, computers, smart watches, smart phones, and the like.

In an embodiment, and with particular reference to FIGS. 10-14, an oral appliance 100 for treatment of sleep apnea in a user is provided. The oral appliance 100 generally includes an upper mouthpiece 102 for positioning over upper dentition of a user, a lower mouthpiece 104 for positioning over lower dentition of the user, an electronic assembly 134 coupled to the upper mouthpiece 102, and a pair of bilateral struts 108, 110 for coupling the upper and lower mouthpieces 102, 104 together. Each of the upper mouthpiece 102 and the lower mouthpiece 104 includes a socket 112, 114 coupled to opposing outer walls thereof. In aspects, the sockets 112, 114 may be monolithically formed with the upper mouthpiece 102 and the lower mouthpiece 104.

Each of the struts 108, 110 includes an elongate first portion 116 having a first projection 118 configured for receipt in the socket 112 of the upper mouthpiece 102, and an elongate second portion 120 extending perpendicularly from the elongate first portion 116 and having a second projection 122 configured for receipt in the socket 114 of the lower mouthpiece 104s. The oral appliance 10, in combination with the struts 108, 110, may be configured to position the bottom jaw of a user in a direction that is forward from the natural position of the user's jaw to aid in the treatment of sleep apnea in the user. The best jaw position for the user may be determined by a dentist and prescribed to a lab that is tasked with fabricating the oral appliance 10. Further details regarding the sockets 112, 114 and the struts 108, 110 may be found in U.S. patent application Ser. No. 17/737,470 filed May 5, 2022, the entire contents of which being incorporated by reference above.

The upper mouthpiece 102 includes a housing 130, a cover 132, and an electronic assembly 134 coupled to the housing 130. The housing 130 has a first portion or occlusal portion 130a (e.g., a top portion) configured to engage an occlusal surface of a user's dentition, and an opposite second portion 130b (e.g., a bottom portion) defining an inner chamber 136. The inner chamber 136 may extend along the entire arcuate length of the upper mouthpiece 102. The second portion 130b of the housing 130 has an outer peripheral edge 138 defining a groove 140, and the cover 132 has an outer peripheral edge or ridge 144 configured for complimentary engagement with the groove 140. The cover 132 of the housing 130 is secured to the second portion 130b of the housing 130 to seal the inner chamber 136 from an external environment. It is contemplated that a sealing mechanism may be provided between at least a portion of the outer peripheral edge or ridge 144 and the groove 140. A biocompatible adhesive may be provided between the groove 140 and ridge 144 to secure the cover 132 and the housing 130 to one another. It is contemplated that the biocompatible adhesive may have sealing capabilities.

The cover 132 has a pair of posterior ends 132a, 132b (FIG. 13) each defining a port 146a, 146b therethrough in communication with the inner chamber 136. In aspects, the second portion 130b of the housing 130 may define ports in posterior ends thereof. The ports 146a, 146b may each have a filter or impermeable mesh cover to prevent fluids or debris from entering the inner chamber 136 while permitting sound to pass therethrough. The upper mouthpiece 102 may include a pair of microphones 148, such as, for example, Micro-Electro-Mechanical Systems ("MEMS") microphones (e.g., the INFINEON MEMS mic), positioned in the inner chamber 136 adjacent the respective ports 146a, 146b. Alternatively, the microphone 148 may be positioned outside of the housing 130. The microphone 148 may be covered and sealed with a biocompatible semi-permeable membrane (e.g., Gore-Tex® waterproof, breathable membrane) to keep moisture and particles away from the MEMS microphone 148. The microphones 148 are configured to detect at least one of the user's normal breathing, changes in the user's breath sound intensity, or the user's snore sound quality. The microphones 148 may be configured to detect upper airway collapse in instances of obstructive sleep apnea. It is contemplated that the microphones 148 may be configured to identify specific breathing patterns associated with sleep-disordered breathing. A printed circuit board 150 may be provided in the inner chamber 136 in addition to other electronic components, including one or more of a pressure sensor, an airflow sensor, a noise detector, an actigraphy sensor, a stimulator, a oxygen saturation (SpO2) sensor, a combined gyroscope and accelerometer, or an electroencephalogram (EEG) sensor.

The microphones 148 may be pre-amplified and configured to record or sample sound at a frequency of about 10 kHz (thereby digitizing the analog sound signal captured). According to an aspect, the microphones 148 are configured to filter signals with:

high pass $\tau=0.004$ s [order 2]; and low pass $\tau=0.0005$ s [order 2], wherein a root-mean-squared (RMS) signal (moving median $\frac{1}{6}$th) is calculated to capture the magnitude of the sound. RMS computes the square root of the mean square of the instantaneous values of the signal. This processing, when applied to each sample of a continuous signal, simply makes all negative values of a signal positive, while keeping positive values as positive. Subsequently, a moving time average may be performed to describe the changes in the RMS signal magnitude over time (i.e. within a breath). Specifically, a moving median may be used, which may describe the median value over a 0.33-second window (window half-width w=0.167 seconds; the output signal at time t is the median value of the input data points from time t−w to t+w seconds).

In at least one configuration, the microphones 148 include a S-VM3000-c Vesper-Mouser.

According to an aspect, the upper mouthpiece 102 includes a processor operably coupled to the microphones 148. The processor in combination with the microphones 148 are configured to identify the user's total sleep time, and total number of sleep disturbances followed by arousals during respiratory events. The microphones 148 are configured to detect changes in the user's air exchange intensity, and the processor is configured to translate the detected changes and trigger a stimulator to stimulate a muscle in the user's oral cavity to reverse the obstruction of the upper airway.

The microphones 148 in combination with the processor are configured to detect at least one of snoring and awake periods or arousal during the user's sleep.

According to an aspect, the upper mouthpiece 102 further includes a storage chip configured to store and record data; and a battery configured to provide power to at least one of the sound measuring device, the processor, and the storage chip. According to an aspect, the data can also be lived streamed and stored externally, if desired by the operator.

Figure 10:
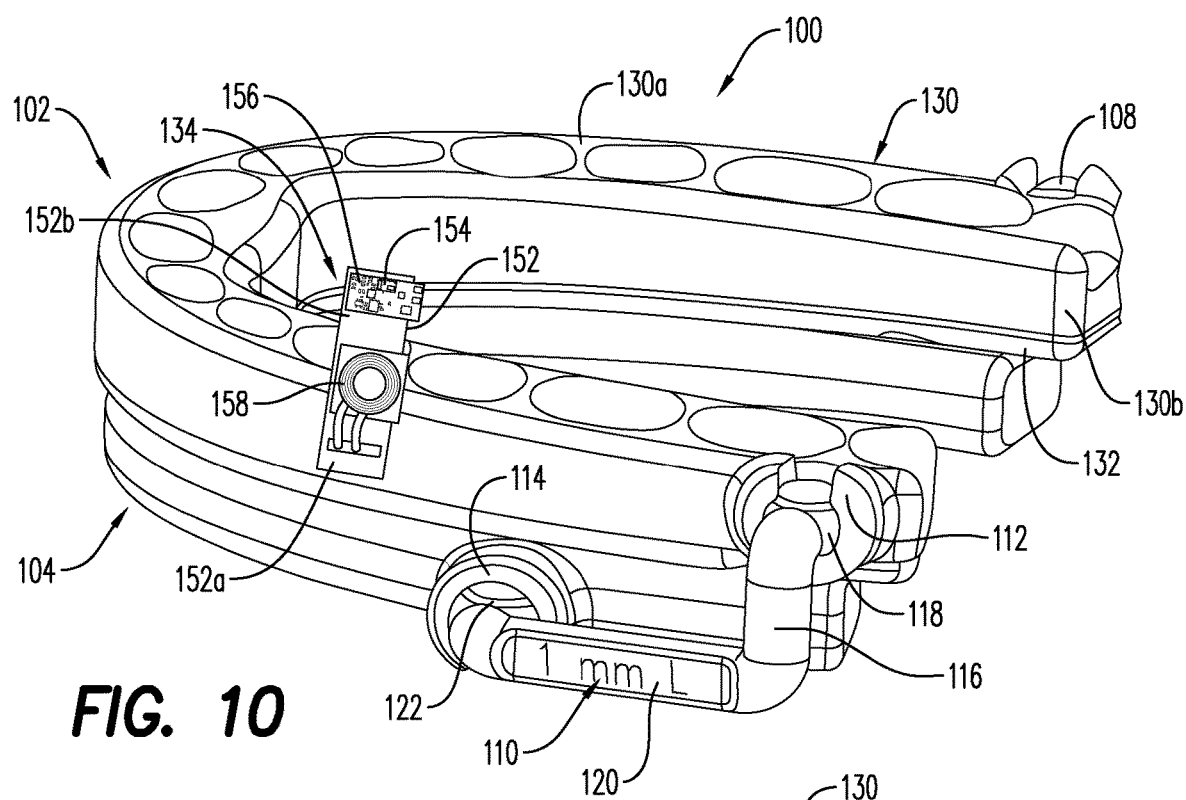
FIG. 10 is a side, perspective view illustrating another aspect of an oral appliance including a top mouthpiece, a bottom mouthpiece, and a strut assembly.
Figure 11:
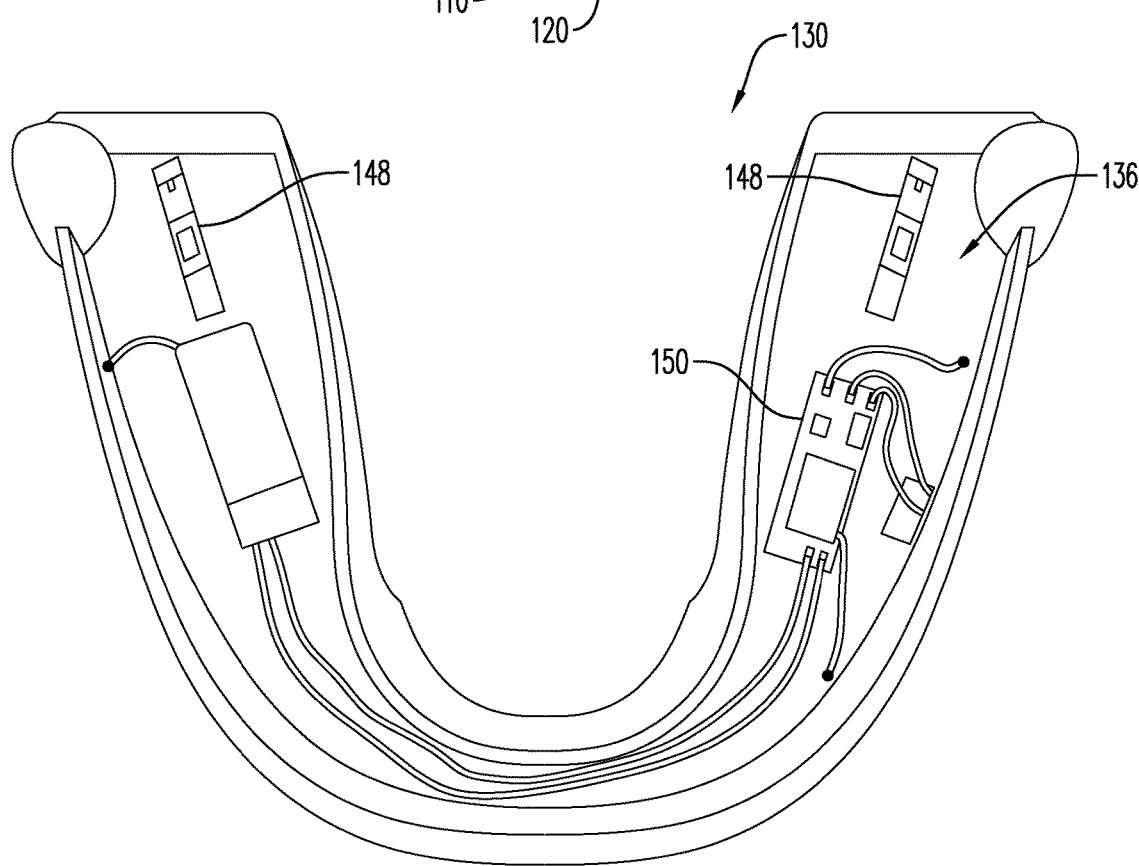
FIG. 11 is a plan view illustrating internal components of the top mouthpiece of the oral appliance of FIG. 10.
Figure 12A:
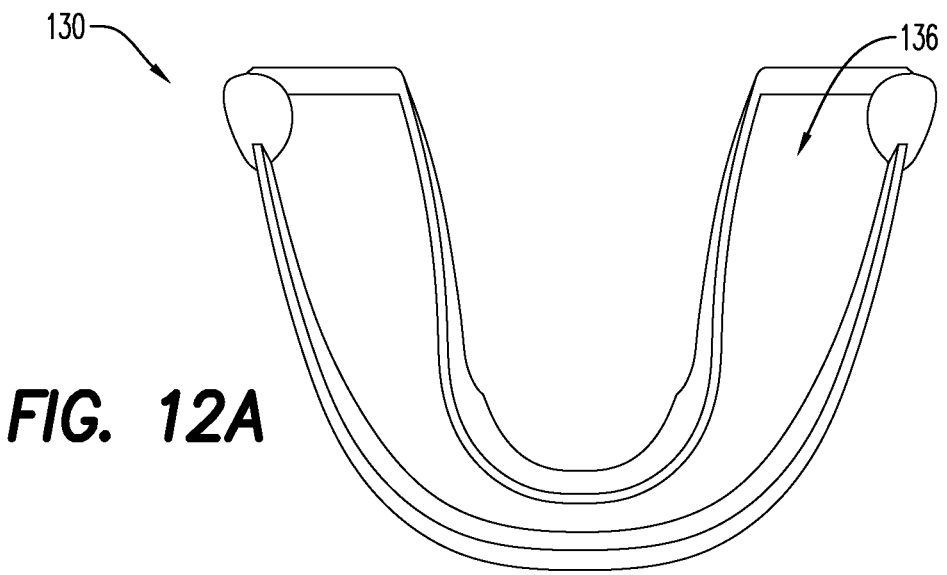
FIG. 12A is a plan view illustrating a housing of the top mouthpiece of FIG. 11.
Figure 12B:
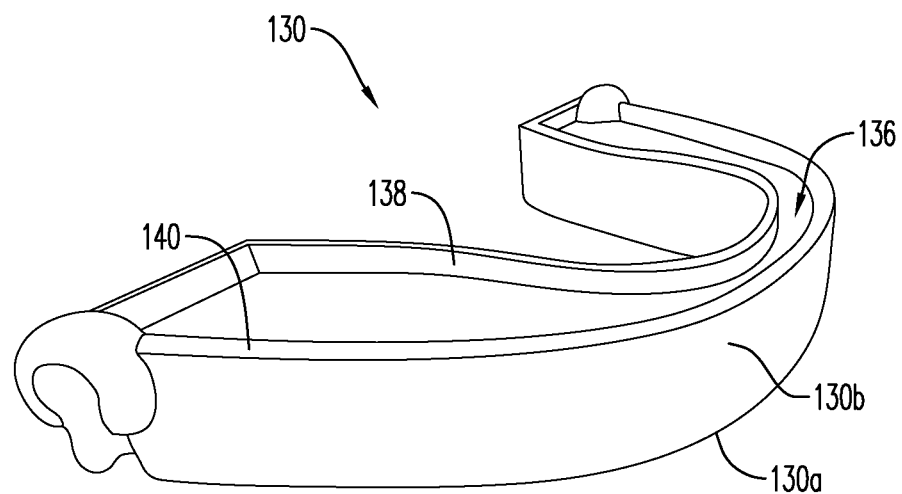
FIG. 12B is a side, perspective view illustrating the housing of FIG. 12A.
Figure 12C:
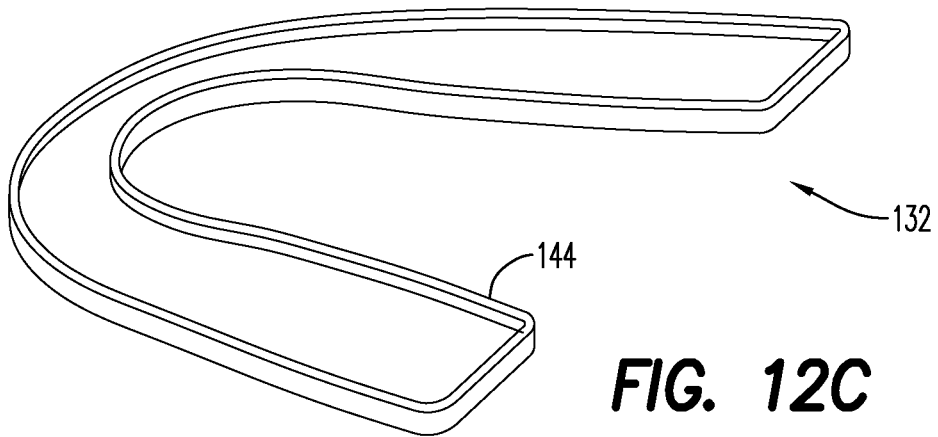
FIG. 12C is a side, perspective view illustrating a cover of the top mouthpiece of FIG. 10.
Figure 13:
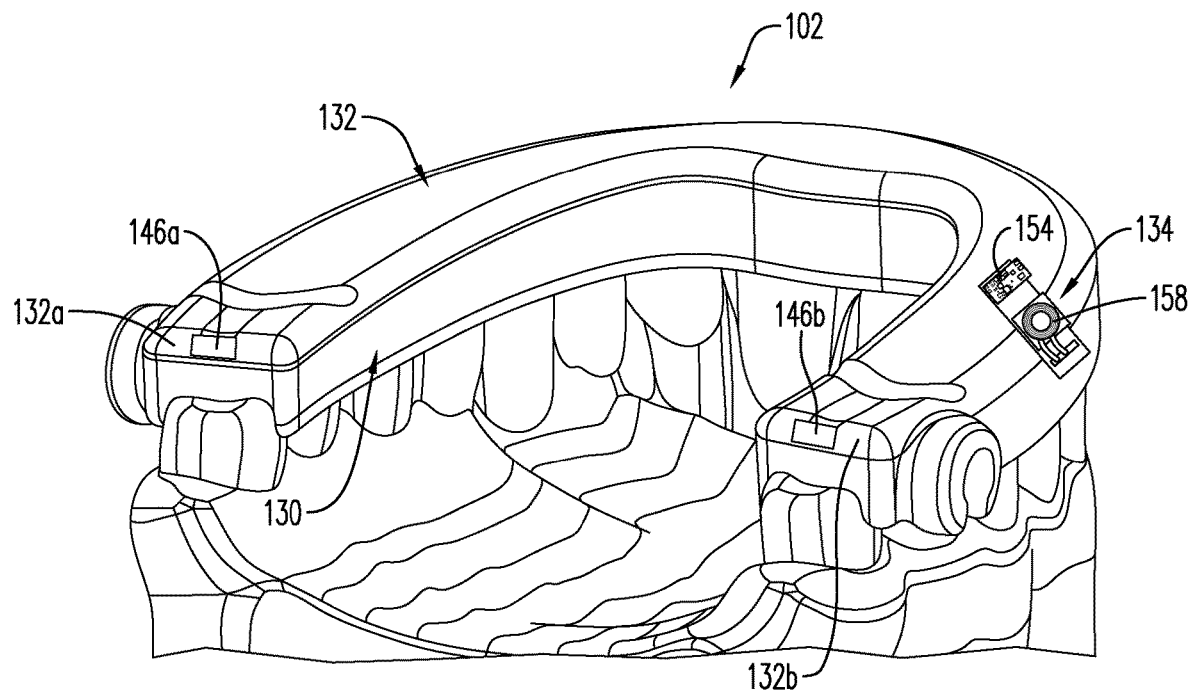
FIG. 13 is a perspective view illustrating the top mouthpiece of the oral appliance of FIG. 10 positioned on a user's upper dentition.
Figure 14:
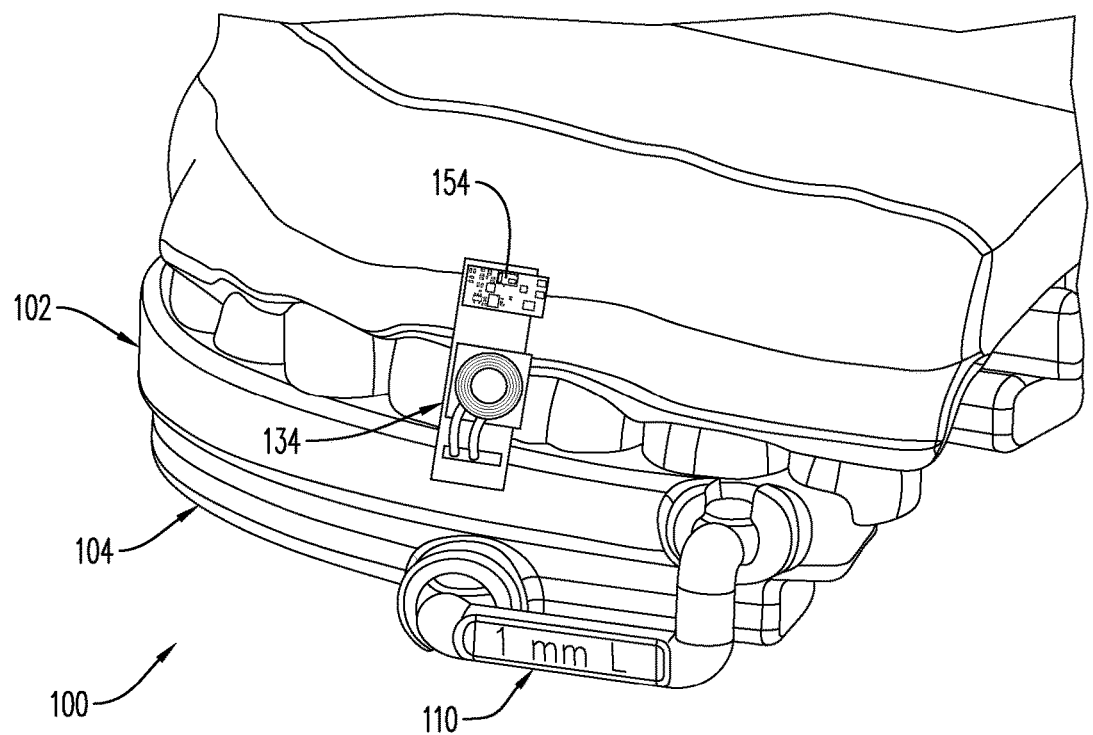
FIG. 14 is a side, perspective view illustrating the oral appliance of FIG. 10 positioned on the upper dentition of the user.

As shown in FIGS. 10, 13, and 14, the electronic assembly 134 may be external to the upper mouthpiece 102 and may extend upwardly from the upper mouthpiece 102. In aspects, the electronic assembly 134 may be encased in a transparent outer housing (not explicitly shown). The electronic assembly 134 includes a substrate 152, an oxygen sensor 154, a printed circuit board 156, an optical housing (not labeled) supported on the printed circuit board 156, and a charging coil 158. The substrate 152 has a first end portion 152a coupled to the housing 130, and a second end portion 152b extending away from the housing 130 in a direction toward gingiva of a user. The first end portion 152a of the substrate 152 is coupled to the housing 130 of the upper mouthpiece 102 and the second end portion 152b of the substrate 152 supports the printed circuit board 156 thereon. The optical housing is supported on the printed circuit board 156 and the oxygen sensor 154 is supported in the optical housing and electrically coupled to the printed circuit board 156. The optical housing may be substantially similar to or identical to the optical housing 56 (FIG. 7) described above.

The oxygen sensor 154 is configured to be oriented toward alveolar mucosa or gingiva of the user to determine an oxygen level of the user. The oxygen sensor 154 may be a reflectance pulse oximeter configured to monitor/sense the oxygen saturation of a user by analyzing the change in color of the user's blood. The reflectance pulse oximeter 154 may measure the pulse rate of the user, typically in beats per minute, based on variations and/or deviations in the user's oxygen saturation. An exemplary pulse oximeter may use light-based technology to sense the actual oxygen saturations of hemoglobin of the user. According to an aspect, the pulse oximeter 154 may be substantially similar to or identical to the pulse oximeter 60 described above.

FIGS. 15-23 illustrate charts that depict the results of sounds that were measuring using a sound measuring device, according to an aspect. The data illustrated in the charts of FIGS. 15-23 was collected at different time intervals of a snoring test utilizing a sound measuring device (e.g., a microphone) of an oral appliance of the present disclosure. The sound measuring device utilized was a microphone embedded in the oral appliance. The sound measuring device utilized was positioned in a sealed circular housing that was open to one side and coupled to an opposing side by an adhesive. The sound measuring device was positioned at a location inferior to one of the user's upper rear molar.

The objective of the tests was to determine whether loud snoring sounds and quiet breathing sounds, as seen at the trachea, would be clearly detectable in the user's mouth with this oral device. The subject, awake, performed a series of inspiratory snoring sounds followed by periods of normal, quiet breathing. The oral microphone signals were captured well-snoring sounds were detected without clipping and breathing sounds were detected above the noise floor.

Figure 15:
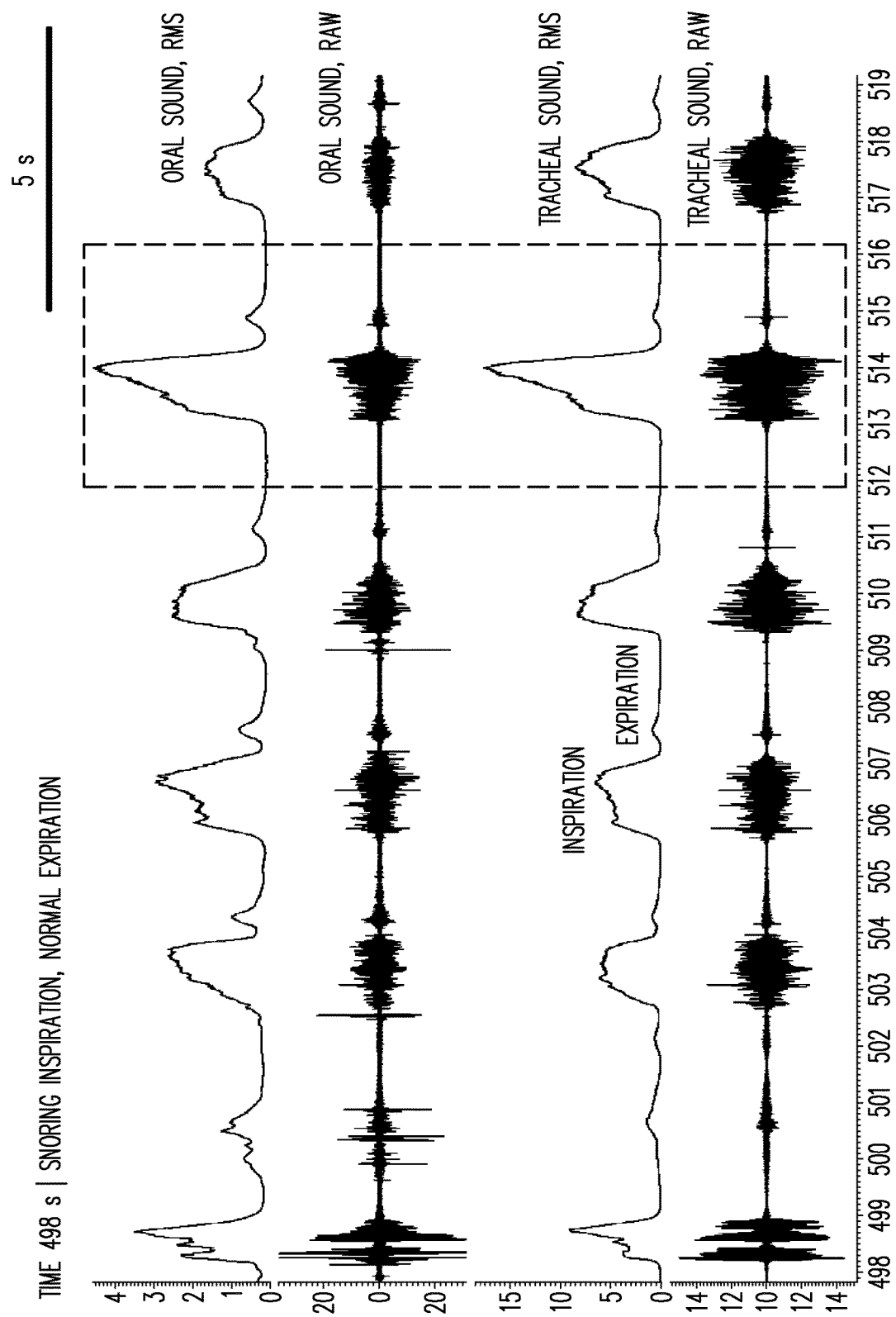
FIG. 15 is a chart that depicts data relating to snoring and normal breathing sounds, collected by a sound measuring device, according to an aspect of the present disclosure.

FIG. 15 is a chart that depicts data relating to snoring and normal breathing sounds, collected by a sound measuring device. As illustrated in the chart, sound was measured starting from about 498 seconds into the user's sleep cycle. The user made snoring sounds on inspiration and breathed normally on expiration. The dashed lines around the 512-516 second marks validates the data collected from the sound measuring device given that the data collected by the sound measuring device of the oral appliance is in line with the illustrated standard reference data from collected from an external (e.g., tracheal) microphone.

Figure 16:
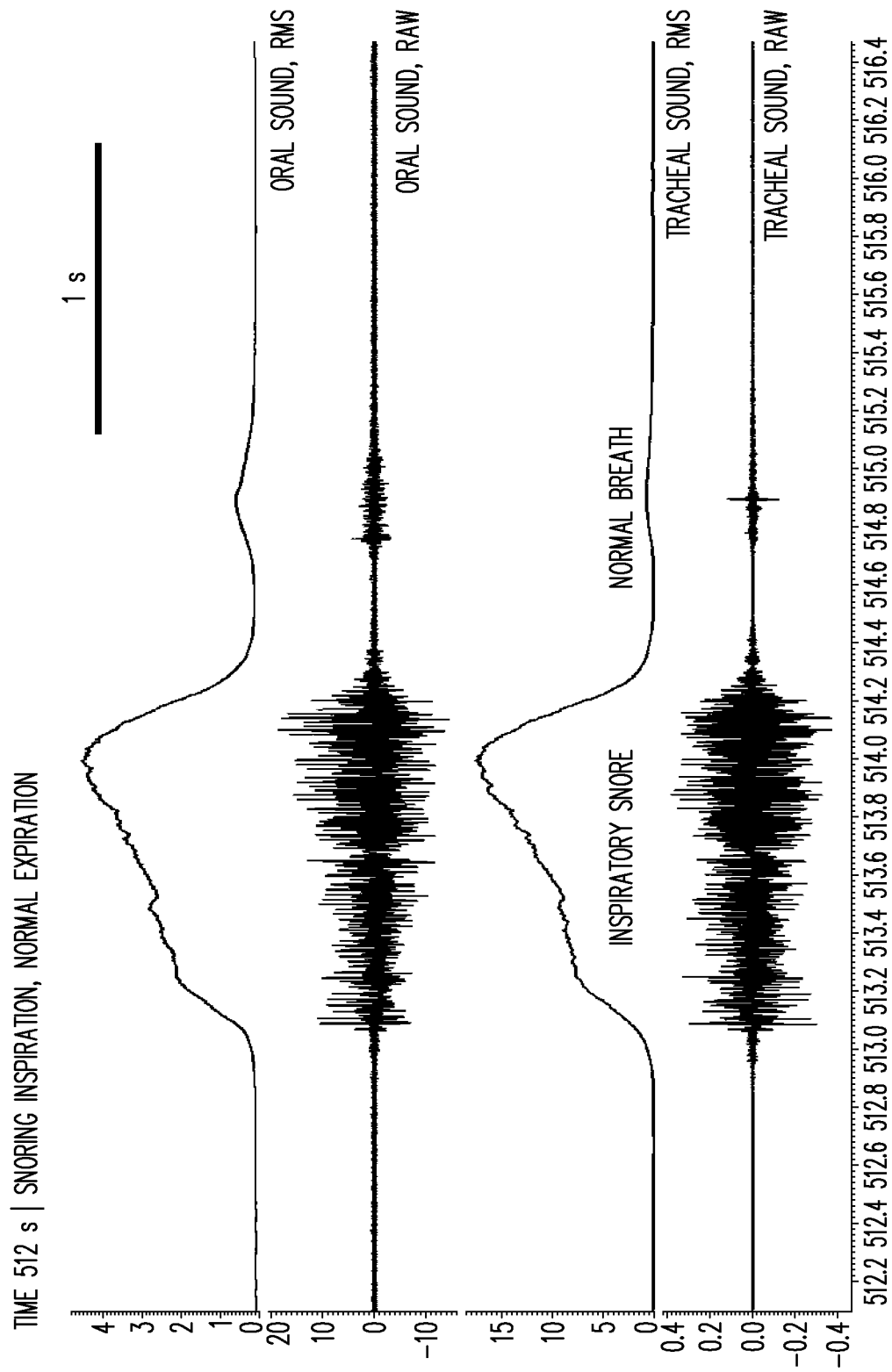
FIG. 16 is a chart that depicts data relating to snoring and normal breathing sounds, collected by a sound measuring device, according to an aspect of the present disclosure.

FIG. 16 is a chart that depicts data relating to snoring and normal breathing sounds, collected by a sound measuring device, according to an aspect. As illustrated in the chart, sound was measured from about 512 seconds into the user's sleep cycle. The user made snoring sounds on inspiration and breathed normally on expiration.

Figure 17:
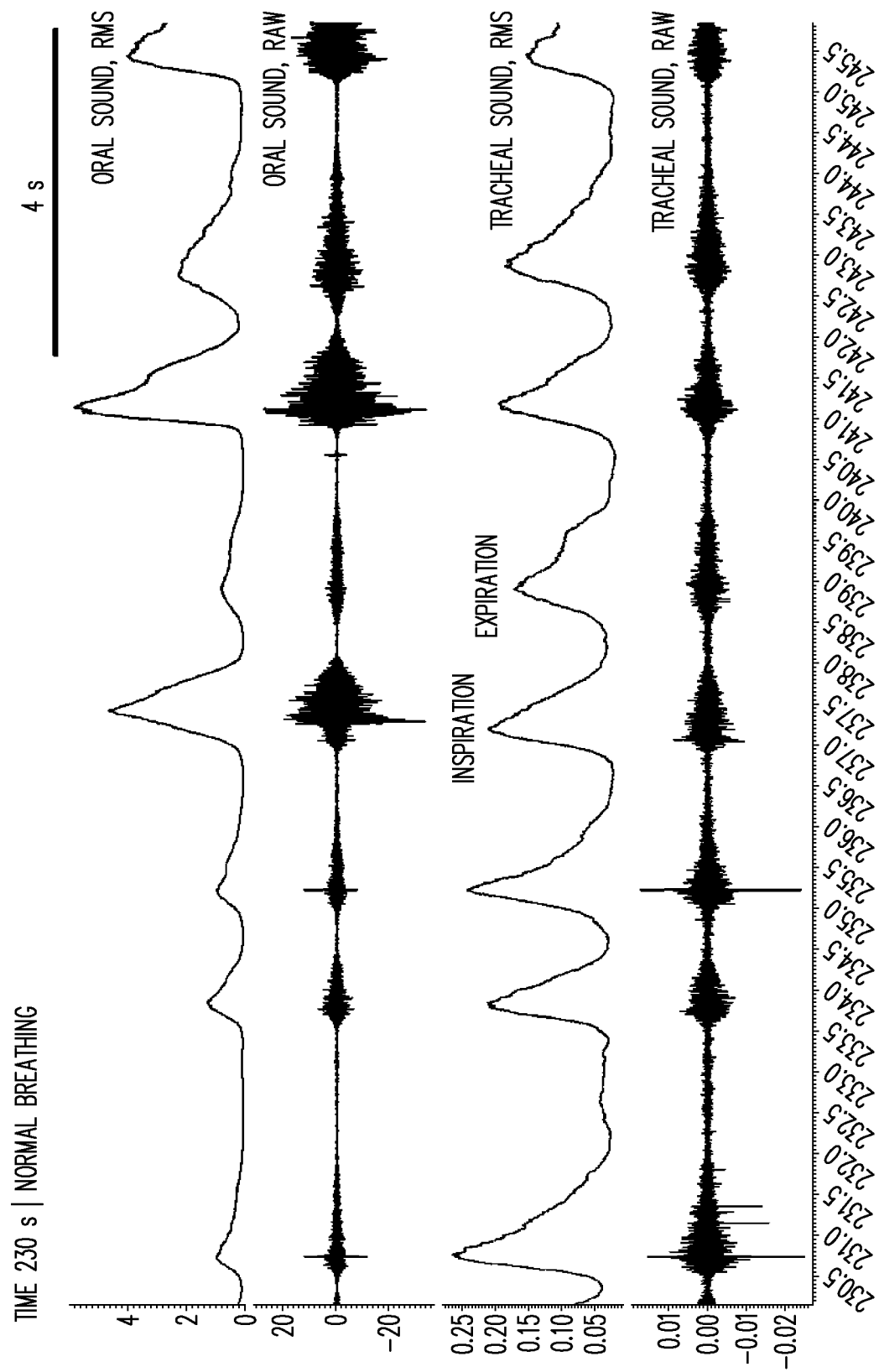
FIG. 17 is a chart that depicts data relating to normal breathing sound, collected by a sound measuring device, according to an aspect of the present disclosure.

FIG. 17 is a chart that depicts data relating to normal breathing sound, collected by a sound measuring device, according to an aspect. As illustrated in the chart, sound was measured from about 230 seconds into the user's sleep cycle. The user breathed normally during that time period without making any sounds.

Figure 18:
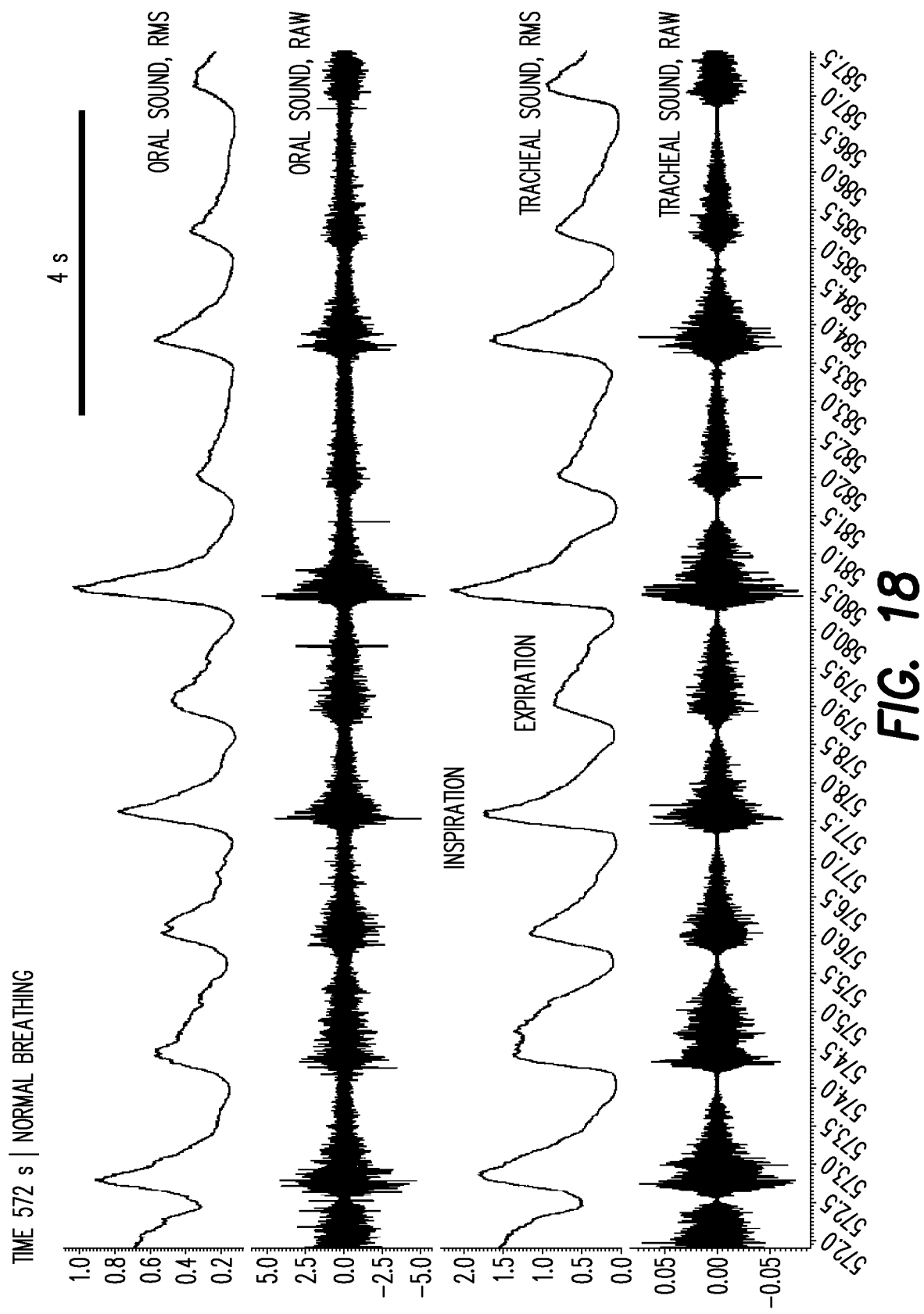
FIG. 18 is a chart that depicts data relating to normal breathing sound, collected by a sound measuring device, according to an aspect of the present disclosure.

FIG. 18 is a chart that depicts data relating to normal breathing sound, collected by a sound measuring device, according to an aspect. As illustrated in the chart, sound was measured from about 572 seconds into the user's sleep cycle. The user breathed normally during that time period.

Figure 19:
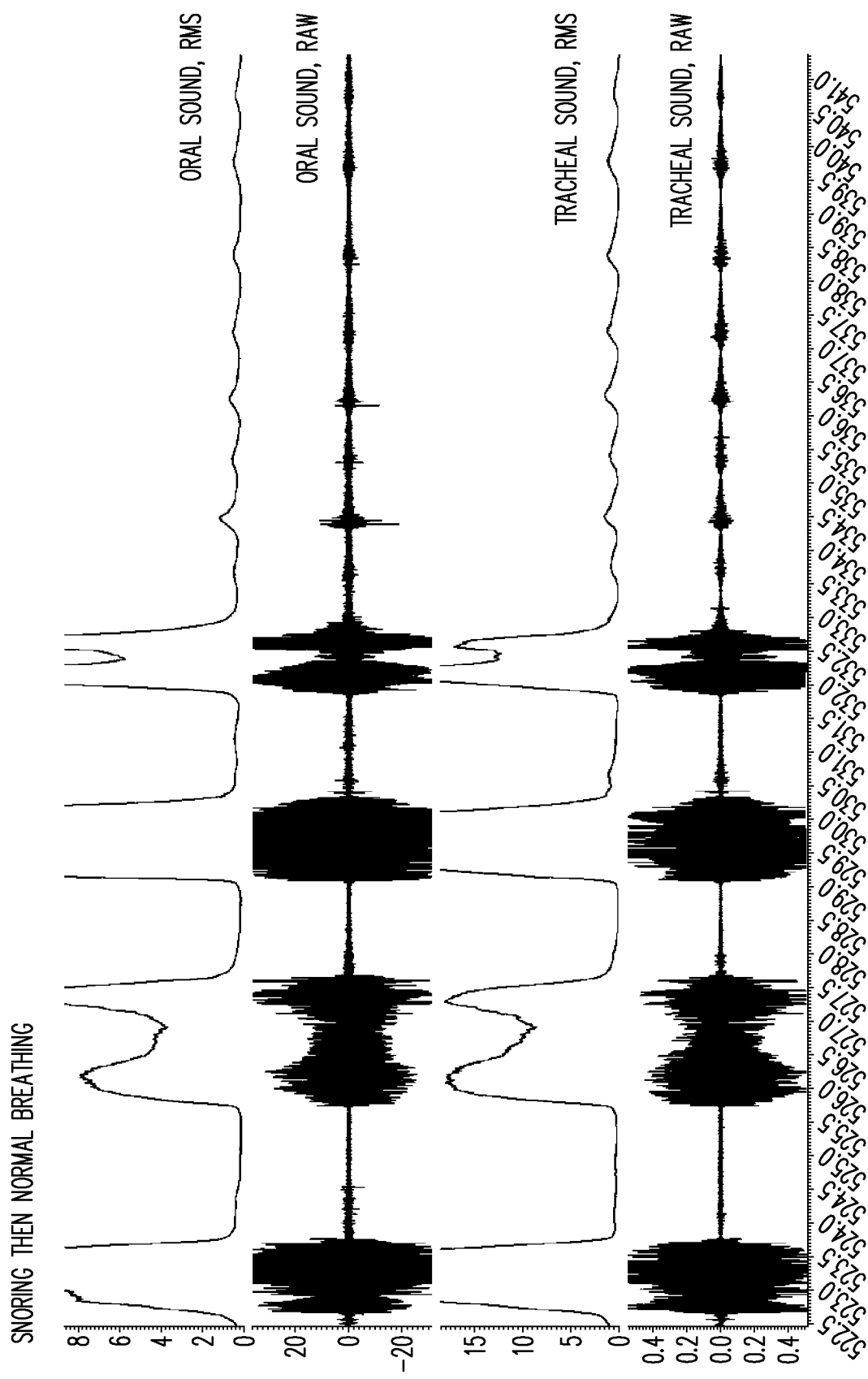
FIG. 19 is a chart that depicts data relating to snoring and normal breathing sounds, collected by a sound measuring device, according to an aspect of the present disclosure.

FIG. 19 is a chart that depicts data relating to snoring and normal breathing sounds, collected by a sound measuring device, according to an aspect. As illustrated in the chart, the user made snoring sounds then breathed normally.

Figure 20:
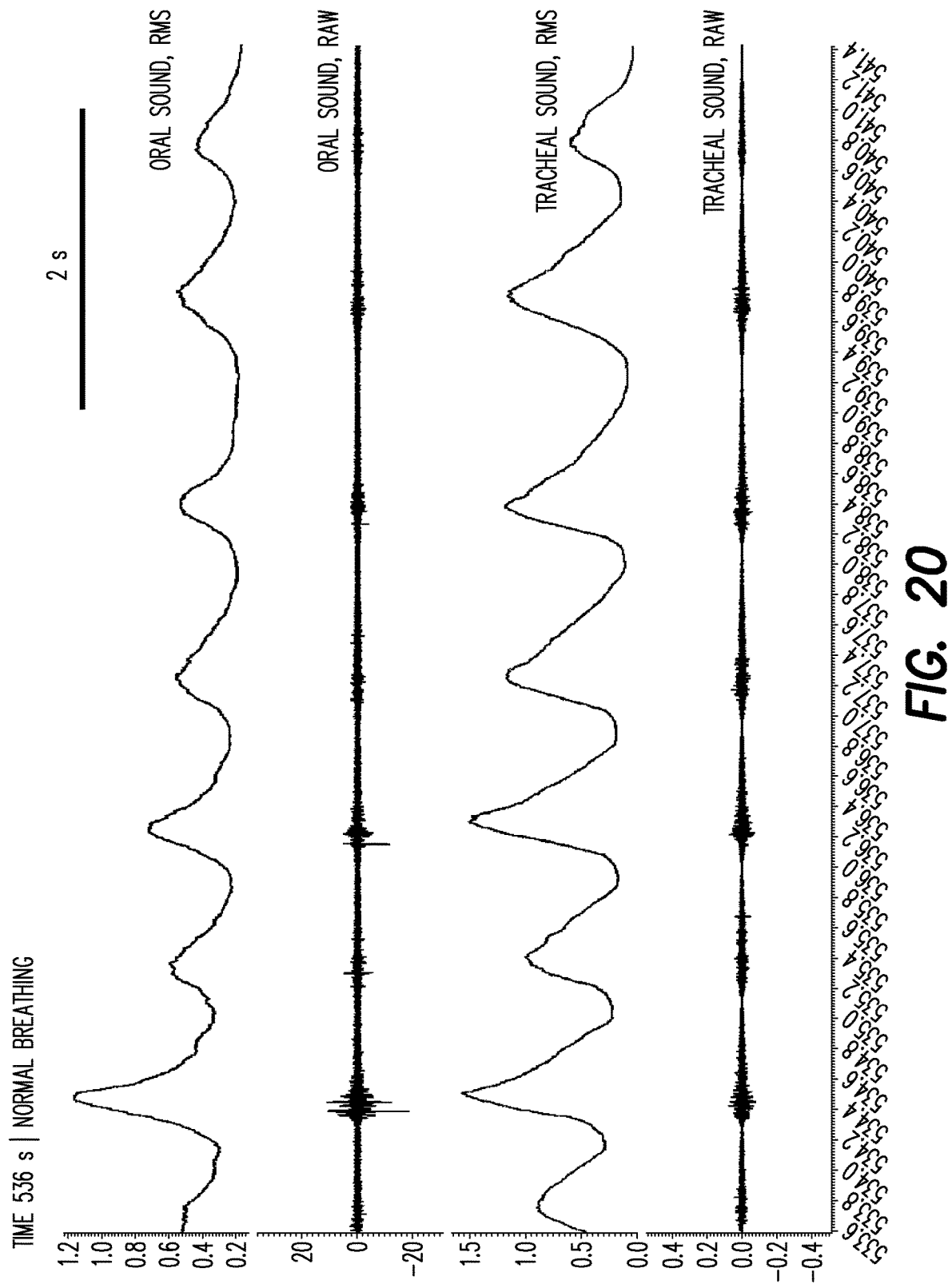
FIG. 20 is a chart that depicts data relating to normal breathing sound, collected by a sound measuring device, according to an aspect of the present disclosure.

FIG. 20 is a chart that depicts data relating to normal breathing sound, collected by a sound measuring device, according to an aspect. As illustrated in the chart, sound was measured from about 533 seconds into the user's sleep cycle. The user breathed normally during that time period.

Figure 21:
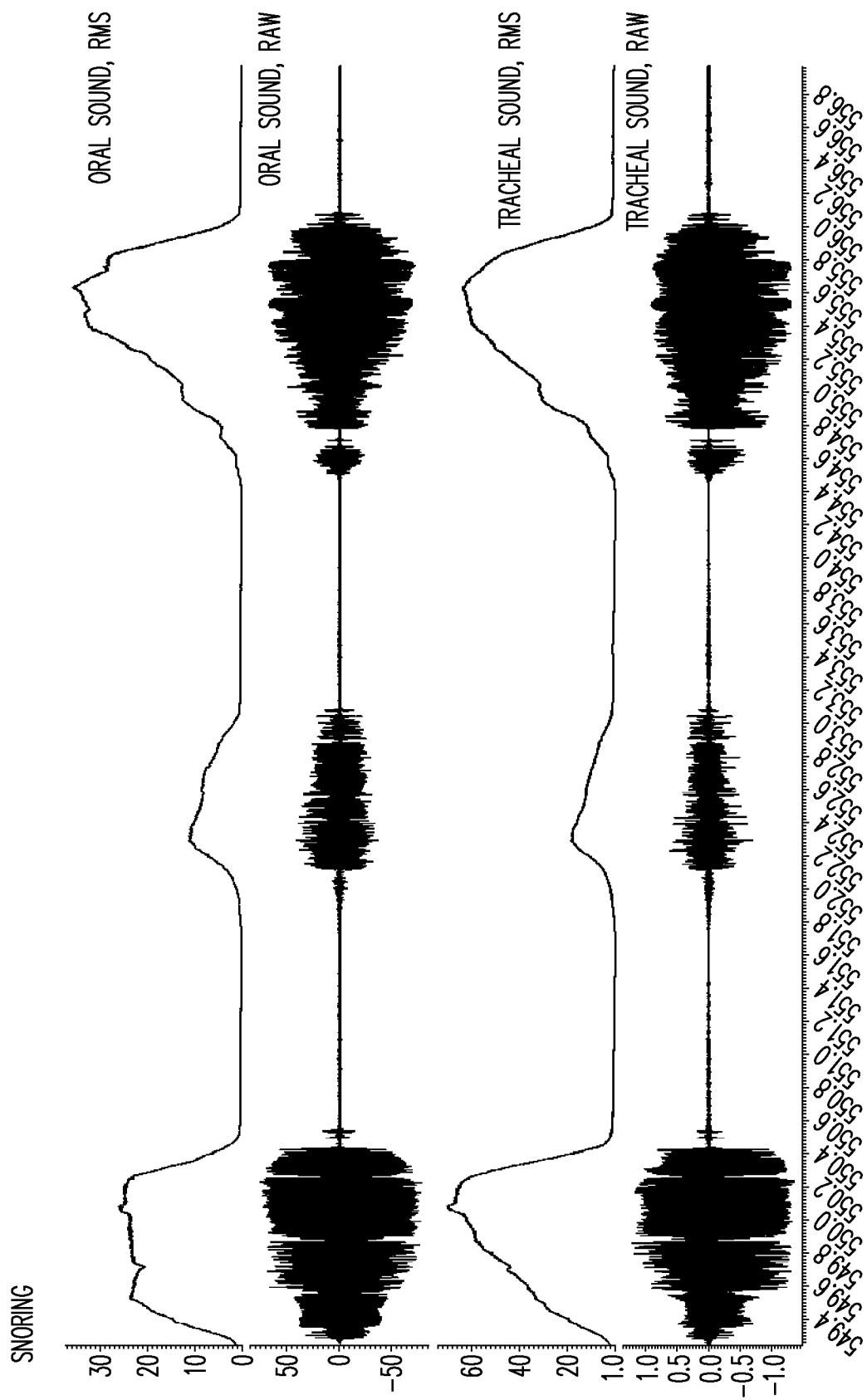
FIG. 21 is a chart that depicts data relating to snoring sounds, collected by a sound measuring device, according to an aspect of the present disclosure.

FIG. 21 is a chart that depicts data relating to snoring sounds, collected by a sound measuring device, according to an aspect. The user made snoring sounds during the test.

Figure 22:
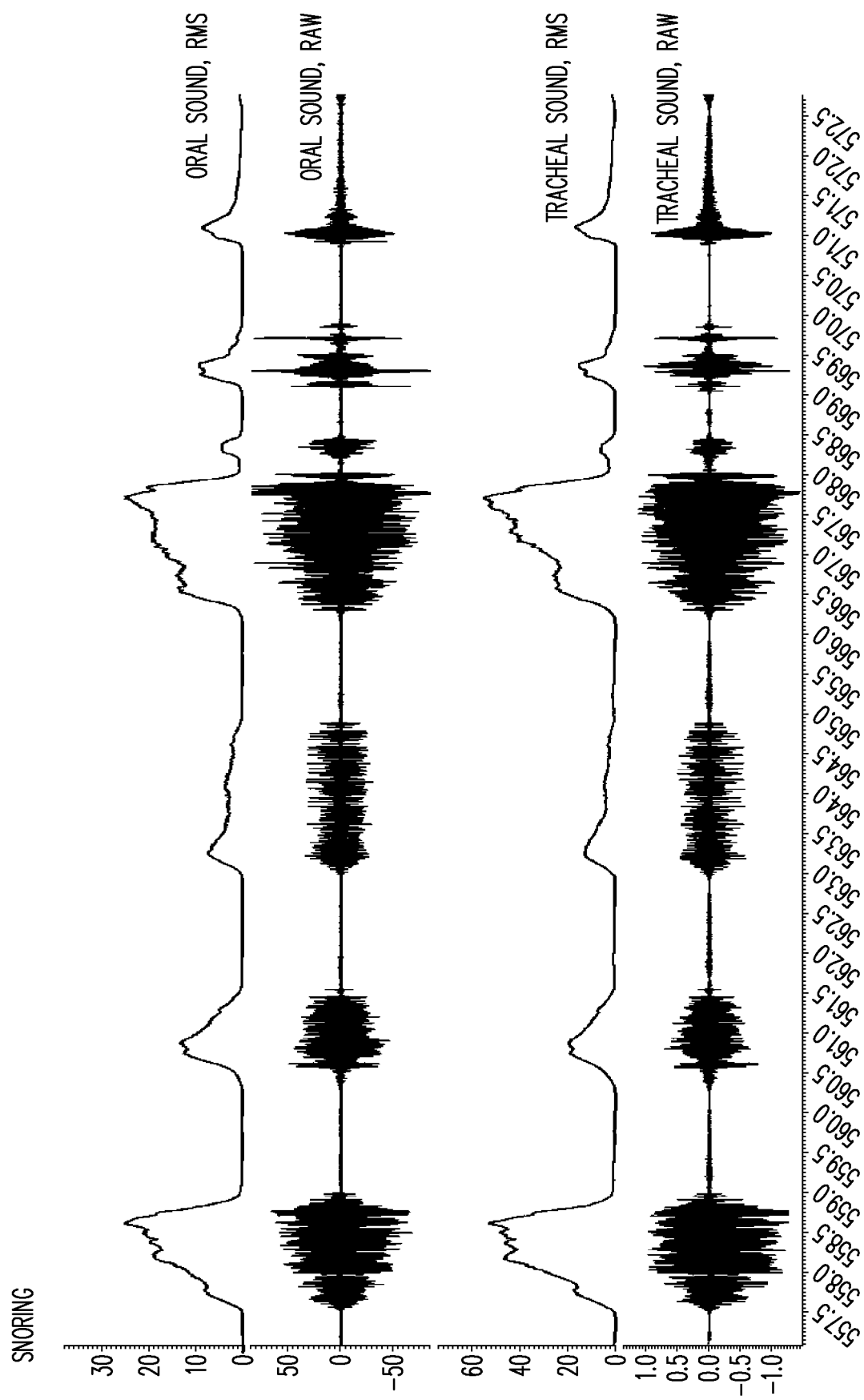
FIG. 22 is a chart that depicts data relating to snoring sounds, collected by a sound measuring device, according to an aspect of the present disclosure.

FIG. 22 is a chart that depicts data relating to snoring sounds, collected by a sound measuring device, according to an aspect. As illustrated in the chart, the user made snoring sounds during the test.

Figure 23:
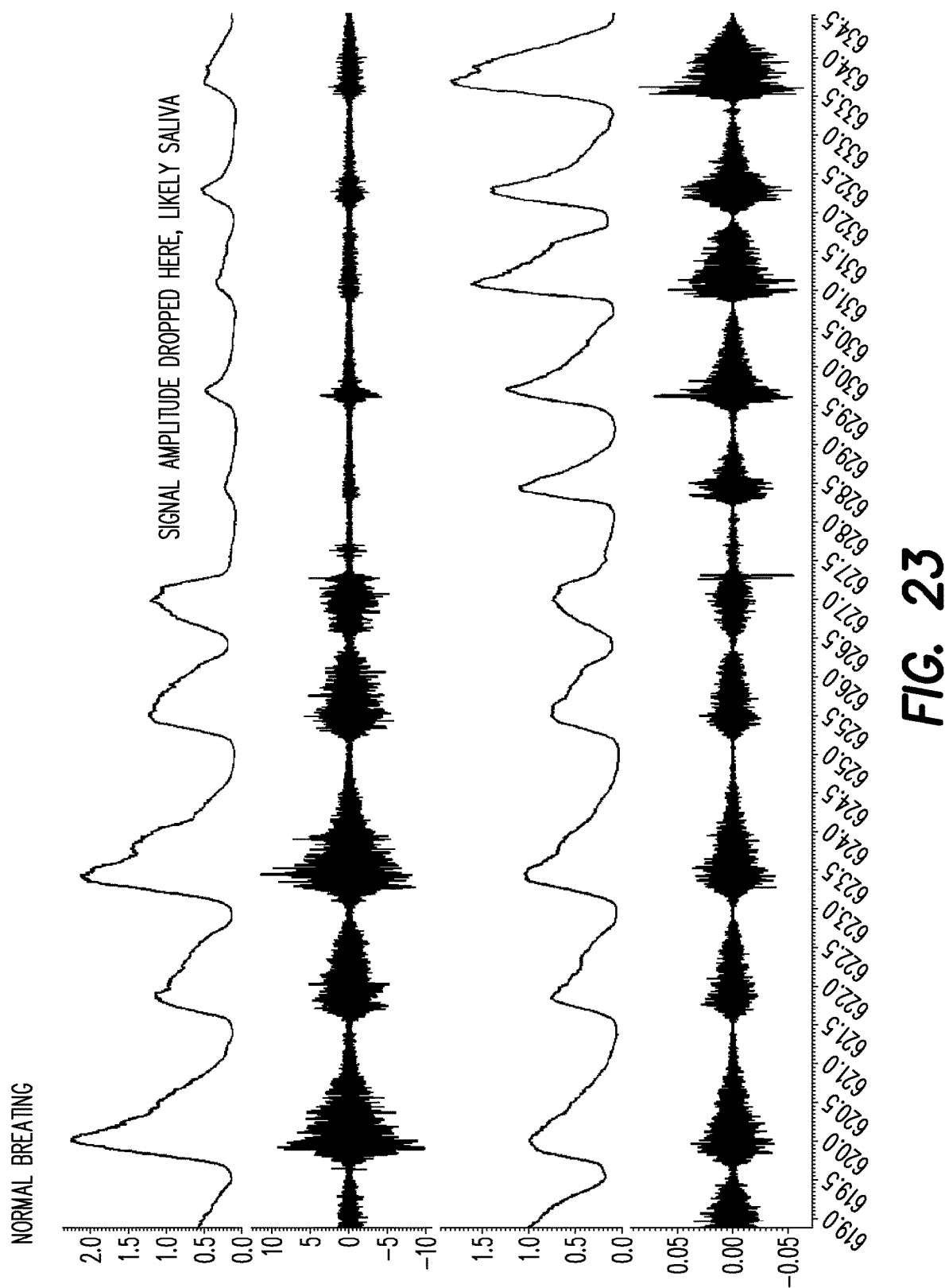
FIG. 23 is a chart that depicts data relating to normal breathing sound, collected by a sound measuring device, according to an aspect of the present disclosure.

FIG. 23 is a chart that depicts data relating to normal breathing sound, collected by a sound measuring device with a signal amplitude dropped due to saliva, according to an aspect. As illustrated in the chart, the user breathed normally during the test.

In aspects, the present disclosure may provide an oral appliance that includes an inertial measuring unit (IMU) (e.g., the BOSCH 6 axis accelerometer, gyroscope) configured to measure triaxial acceleration and triaxial angular velocity. According to an aspect, the IMU includes a gyroscope and an accelerometer. The gyroscope is configured to output angular velocity signals on three axes in space, while the accelerometer is configured to output linear acceleration signals on three axes in space. According to an aspect, the IMU is a miniature IMU sized so that it can be coupled to the mouthpiece. The miniature IMU may be secured to a buccal, lingual, or occlusal wall of the mouthpiece. The placement of the IMU or miniature IMU may be at the most anterior segment of the user's lower jaw (that is, the location of the user's lower front incisors). It is contemplated that this may an optimal location on the mouthpiece at least because this anatomical location will likely express the most detailed movement during recording. This follows the physics law of "the fulcrum effect". The closer the point of effort is to the fulcrum (the back of the jaw where the joints and associated muscles and ligaments are), the less effort it will take for the movement at the farthest point to the fulcrum (most anterior part of the jaw)-hence the more sensitive that point is to detecting movement.

It is contemplated that the oral appliance may be configured for the detection of lower jaw movements. These lower jaw movements may serve as a surrogate bio-signal for the detection of breathing effort, including snoring and arousal during sleep. According to an aspect, the lower jaw movements may be in addition to other bio-signals that are indicative of the presence of sleep apnea in a user. Jaw movement bio-signals can identify specific breathing patterns associated with sleep-disordered breathing, including obstructive sleep apnea ("OSA") The use of the oral appliance including the IMU or miniature IMU can indicate sleep vs awake stage, and can determine OSA severity levels in those patients. Further analysis using specific algorithms can also identify total sleep time, total number of sleep disturbances followed by arousals during respiratory events or OSA events. According to an aspect, the algorithm may also be used as a predictive model for future systemic issues such as cardiovascular disease (CVD). It is contemplated that the IMU or accelerometer-gyroscope combination may determine jaw clenching and grinding which is an indicator for arousals during periods of disturbed sleep. The IMU may also be an indicator of treatment compliance for a patient undergoing treatment for OSA.

FIGS. 24A-26B include data collected by an IMU as described above.

Figure 24A:
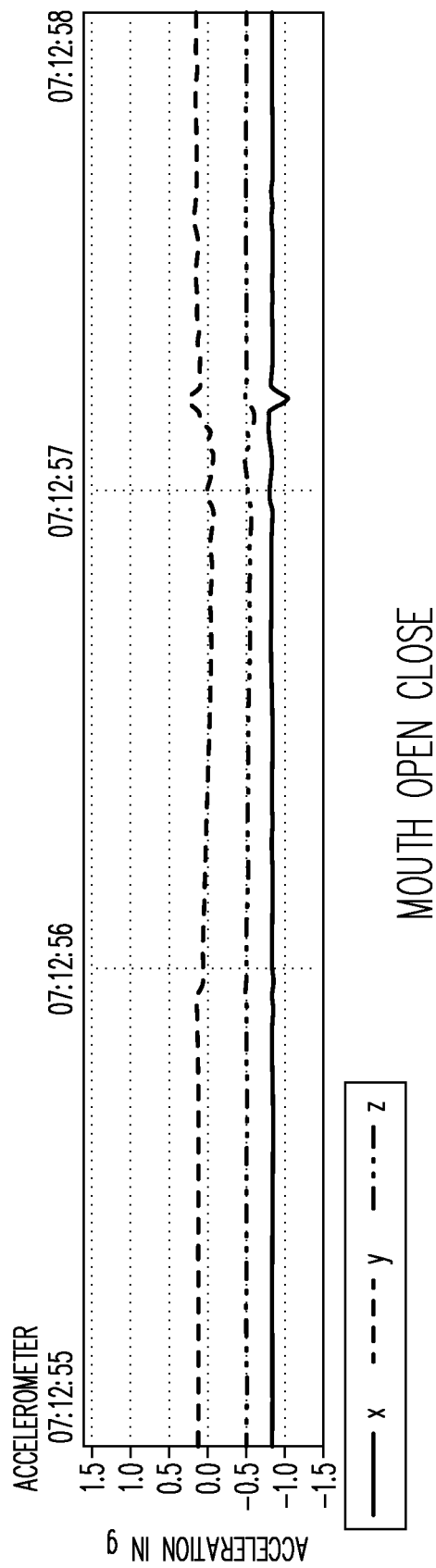
FIG. 24A are two charts illustrating data collected by additional sensors such as an accelerometer and a gyroscope of an oral appliance of the present disclosure with a patient with an open mouth and an inertial measuring unit (IMU) intra-orally coupled to the oral appliance.
Figure 24A:
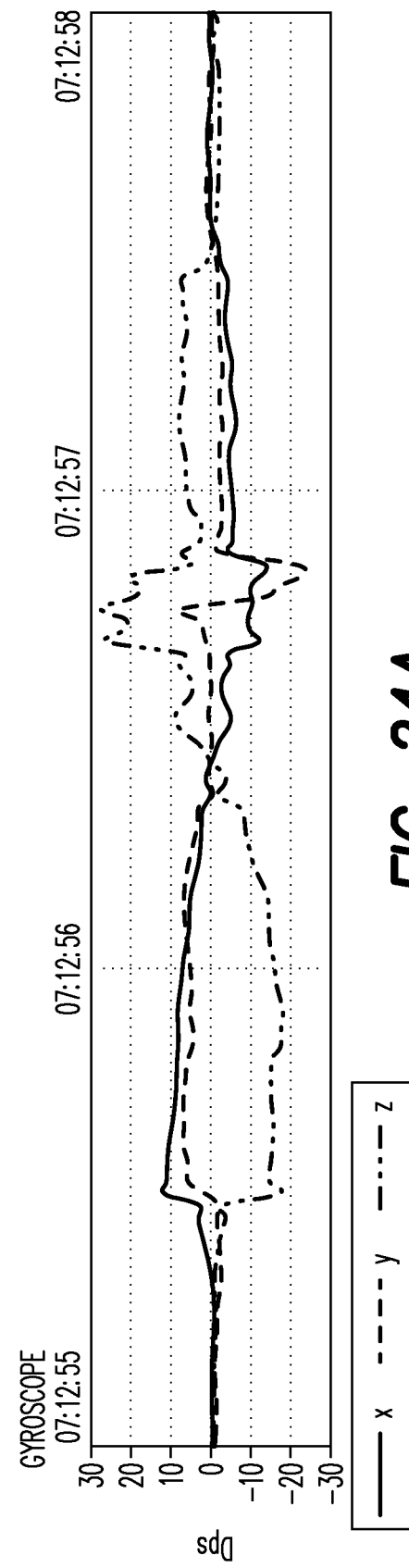
Figure 24B:
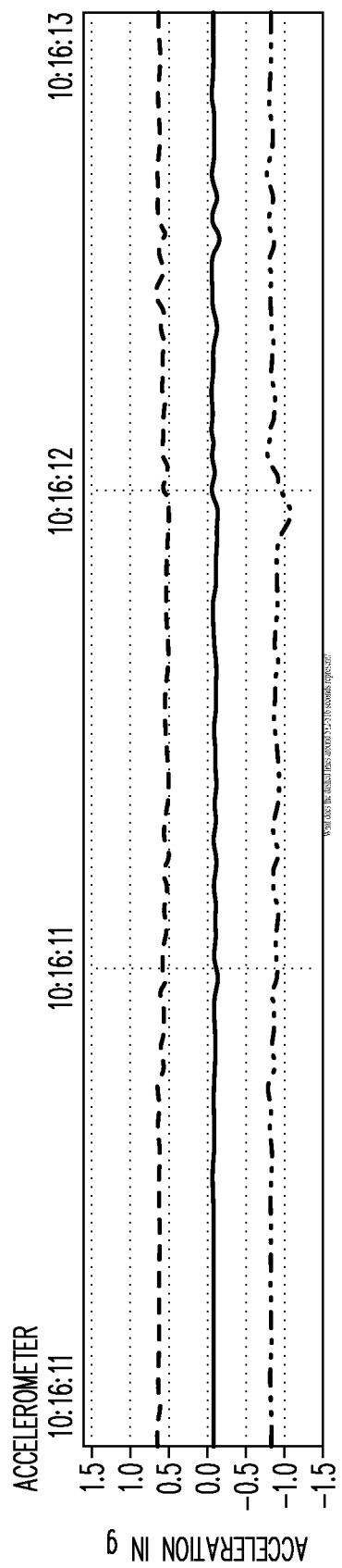
FIG. 24B are two charts illustrating data collected by an accelerometer and a gyroscope of an oral appliance of the present disclosure with a patient with an open mouth and an IMU extra-orally coupled to the patient's chin.
Figure 24B:
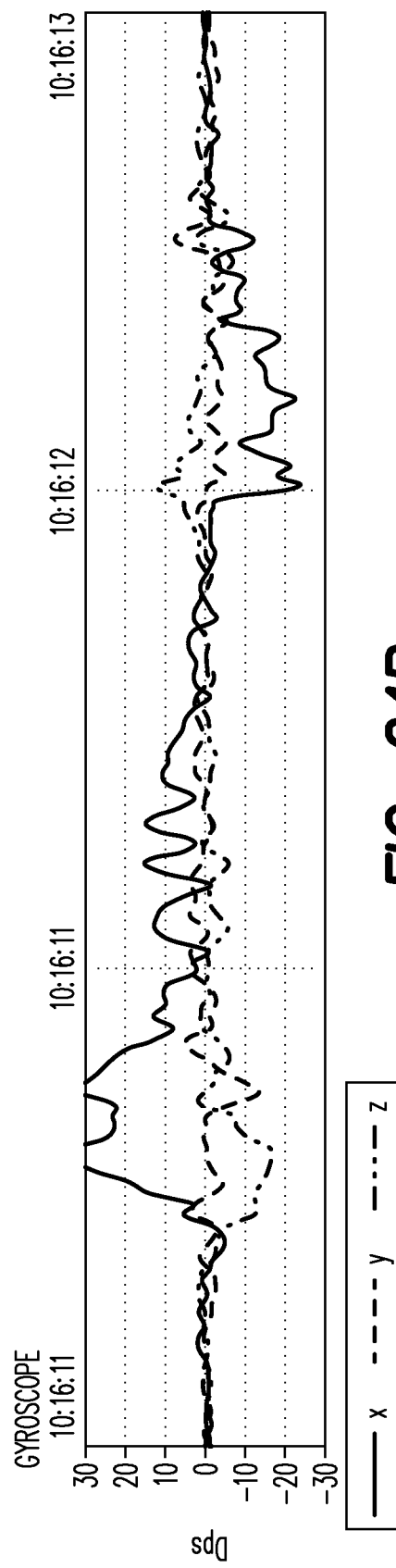

FIGS. 24A and 24B compare data collected by an IMU coupled to an oral appliance of the present disclosure with data collected by an IMU extra-orally coupled to the patient's chin, where a patient is opening and closing their mouth and their head is in a straight supine position. This data may be important in determining whether the patient is a "mouth breather" during sleep and the extent of their mouth breathing.

Figure 25A:
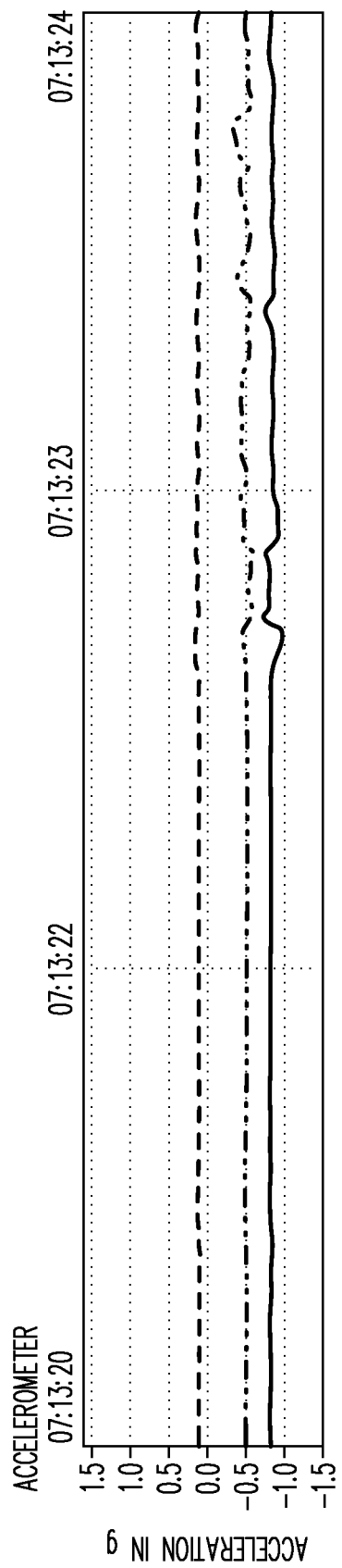
FIG. 25A are two charts illustrating data collected by an accelerometer and a gyroscope of an oral appliance of the present disclosure with a patient grinding their teeth in a side-to-side motion and an IMU intra-orally coupled to the oral appliance.
Figure 25A:
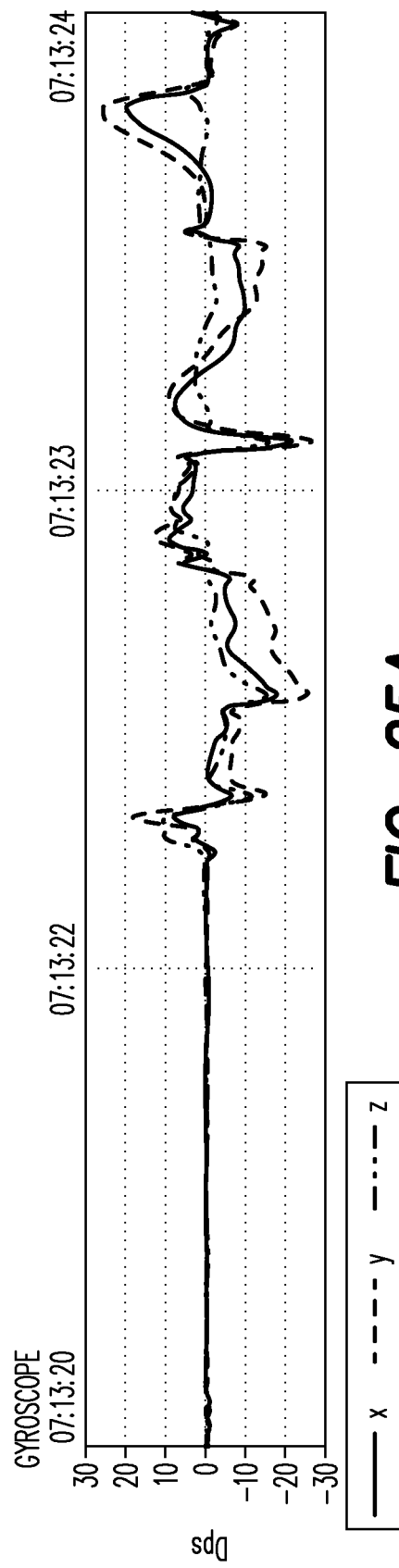
Figure 25B:
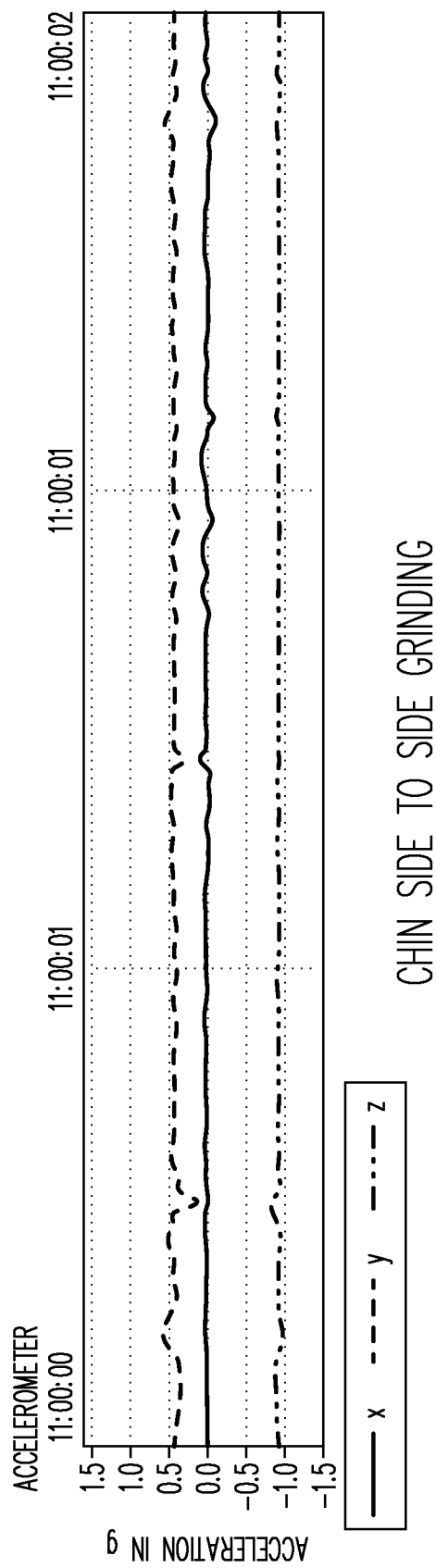
FIG. 25B are two charts illustrating data collected by an accelerometer and a gyroscope of an oral appliance of the present disclosure with a patient grinding their teeth in a side-to-side motion and an IMU extra-orally coupled to the patient's chin.
Figure 25B:
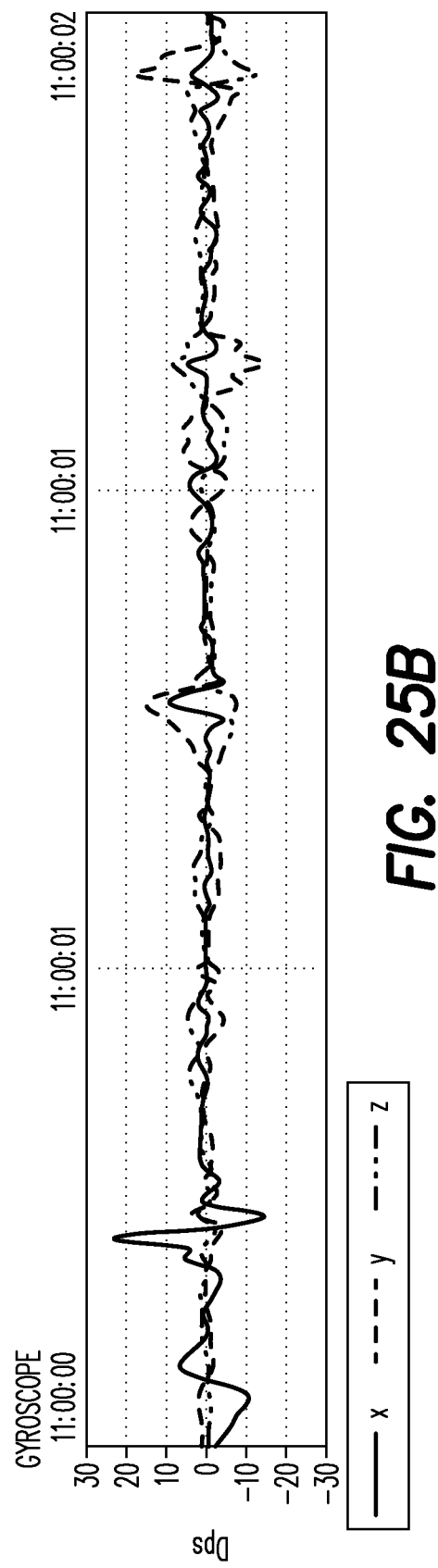

FIGS. 25A and 25B compare data collected by an intra-oral IMU coupled to an oral appliance of the present disclosure with data collected by the IMU extra-orally coupled to the patient's chin, where a patient is grinding their teeth in a side-to-side motion and their head is in a straight supine position. This data may provide an indication of sleep bruxism secondary to obstructive sleep apnea.

Figure 26A:
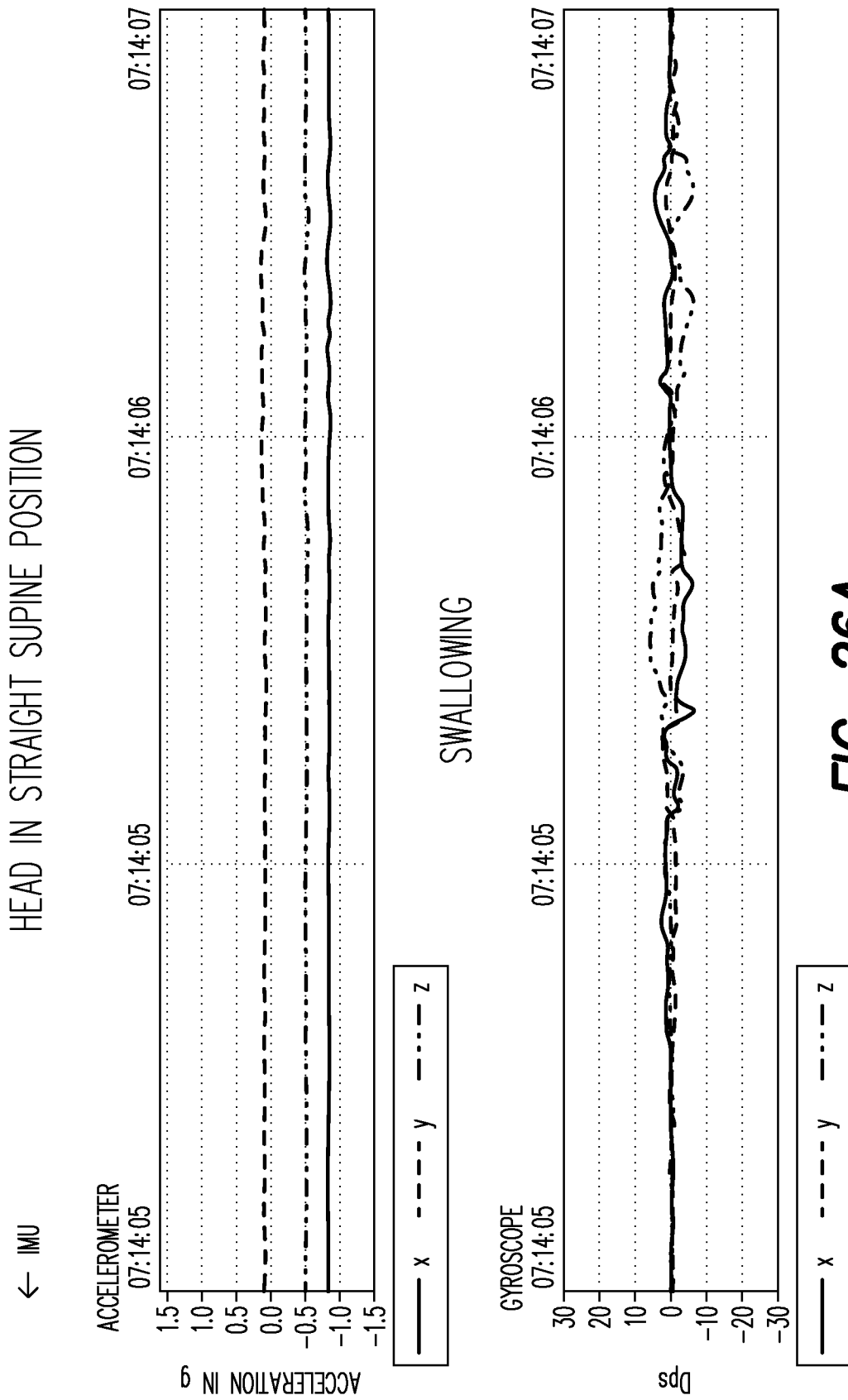
FIG. 26A are two charts illustrating data collected by an accelerometer and a gyroscope of an oral appliance of the present disclosure with a patient swallowing and an IMU intra-orally coupled to the oral appliance.
Figure 26B:
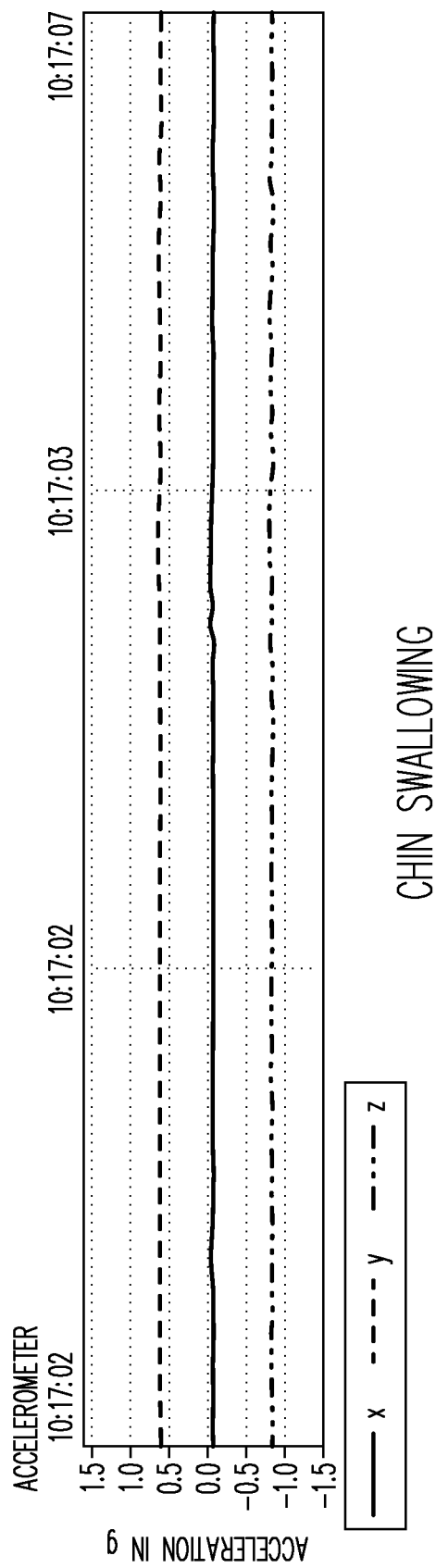
FIG. 26B are two charts illustrating data collected by an accelerometer and a gyroscope of an oral appliance of the present disclosure with a patient swallowing and an IMU extra-orally coupled to the patient's chin.
Figure 26B:
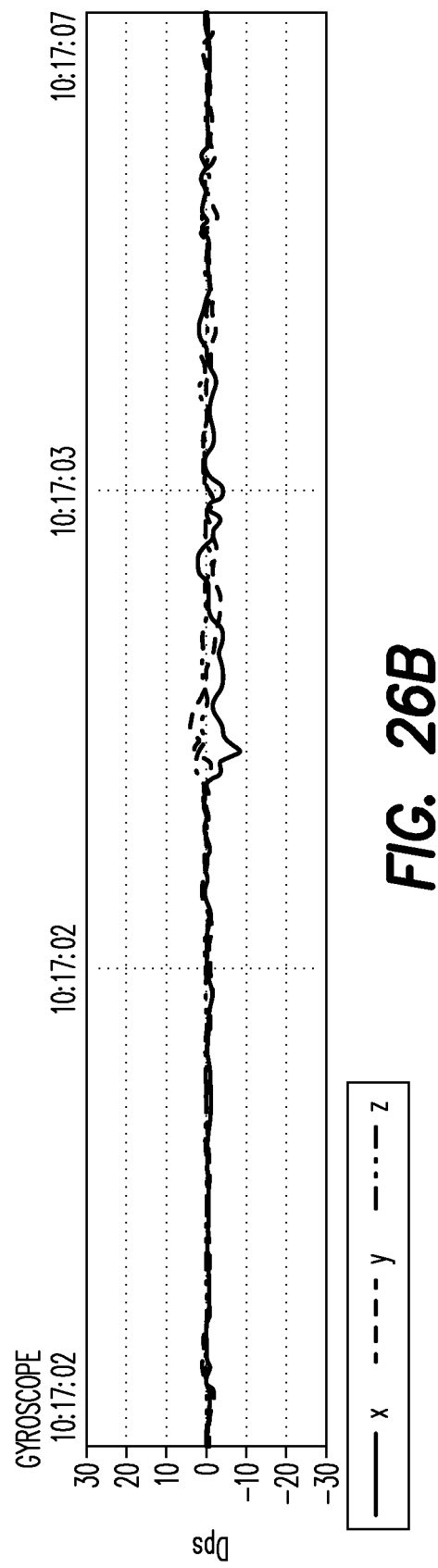
Figure 27:
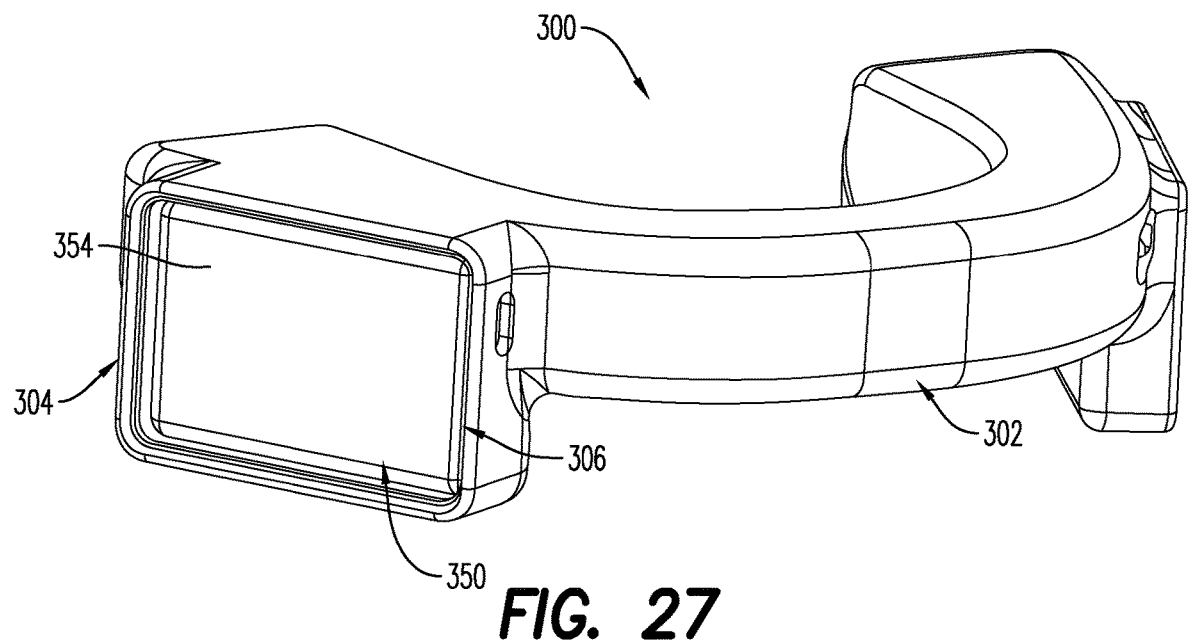
FIG. 27 is a perspective view illustrating yet another embodiment of an oral appliance including a sensor assembly.
Figure 28:
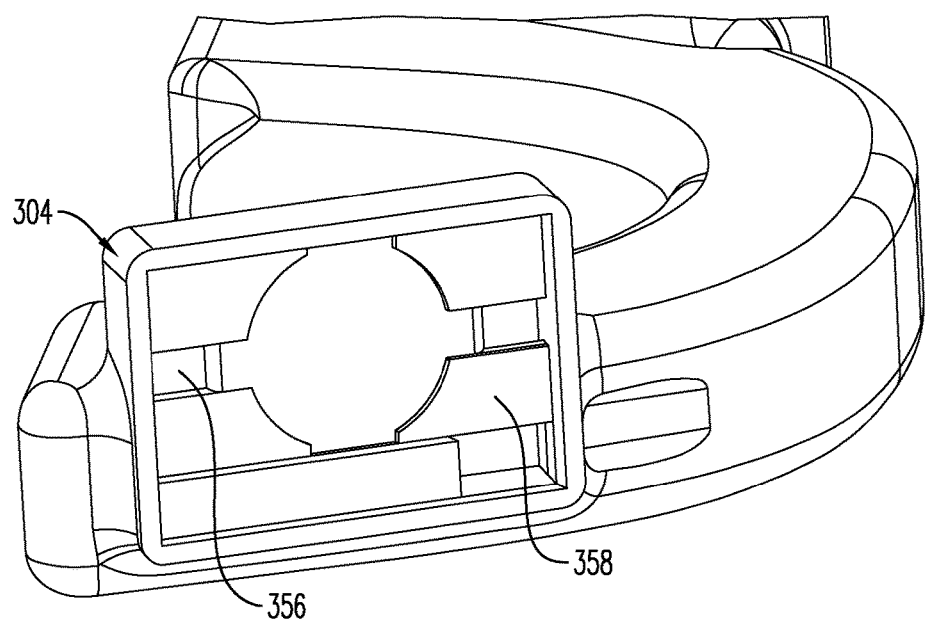
FIG. 28 is a partial, perspective view illustrating the sensor assembly of FIG. 27 with a charging coil thereof removed.
Figure 29:
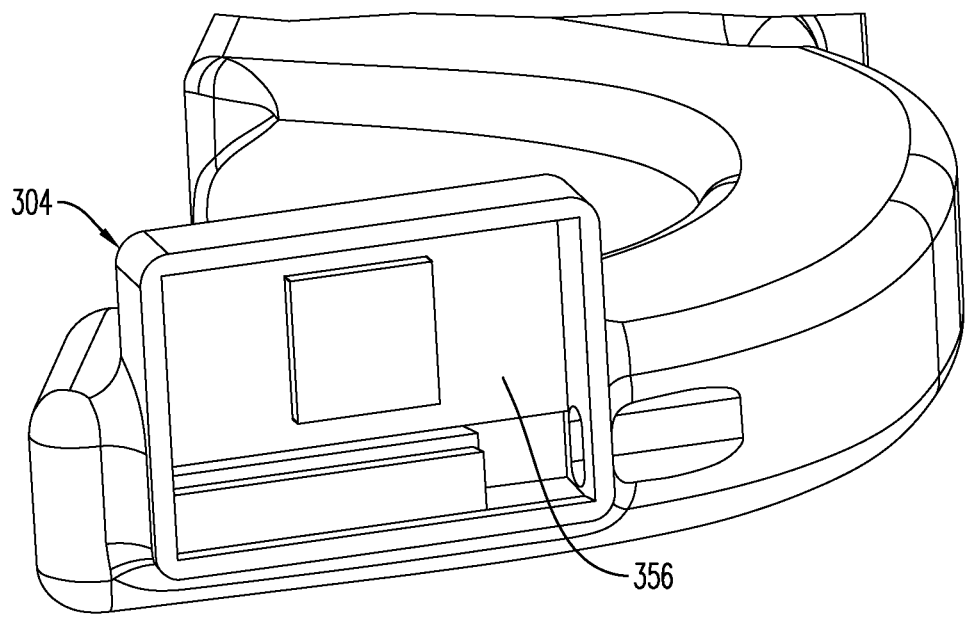
FIG. 29 is a partial, perspective view illustrating the sensor assembly of FIG. 27 with the charging coil and a spacer thereof removed.
Figure 30:
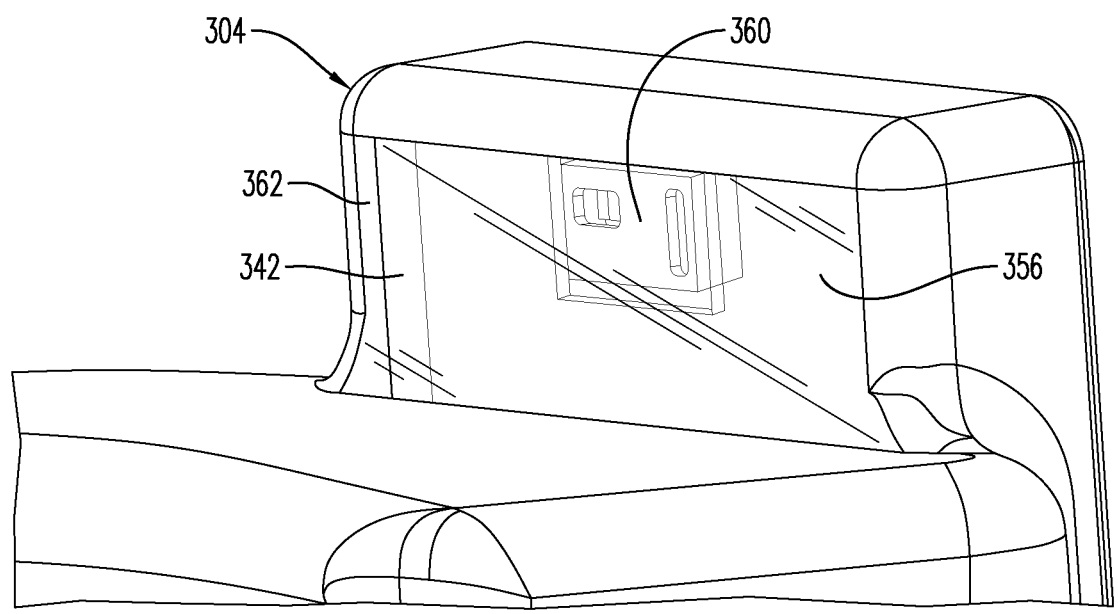
FIG. 30 is another partial, perspective view illustrating a printed circuit board and a sensor of the sensor assembly of FIG. 29 positioned in the housing.

FIGS. 26A and 26B compare data collected by an IMU coupled to an oral appliance of the present disclosure with data collected by the IMU extra-orally coupled to the patient's chin, with a patient swallowing.

Swallowing is a strong indicator of arousal during sleep, most frequently occurring in REM. The intra-oral IMU of the present disclosure has a very distinct and consistent wave shape during swallowing, compared to the external chin sensor.

With reference to FIGS. 27-30, another embodiment of an oral appliance 300 is provided, similar to the oral appliances 10, 100, 200 described above. The oral appliance 300 generally includes a mouthpiece 302 and a sensor assembly 350 positioned in an appendage or box 304 extending perpendicularly away from a posterior end portion of the mouthpiece 302. The sensor assembly 350 may be positioned adjacent an optical window 342 (FIG. 30) of the appendage 304 and includes a charging coil 354, a printed circuit board 356, a spacer 358, and an oxygen sensor 360. The oxygen sensor 360 may be oriented on a sagittal plane of the user's oral cavity and towards buccal gingiva of the user when the oral appliance 300 is worn by the user. The oxygen sensor 360 may be similar to any of the oxygen sensors described above.

The charging coil 354 is stacked over the printed circuit board 356 and separated from the printed circuit board 356 by the spacer 358 to reduce heat that is produced by the charging coil 354 during charging. As such, the spacer 358 keeps excess heat away from the printed circuit board 356. The appendage 304 is specially designed to allow for the charging coil 354 to be housed in a recessed part 306 of the appendage 304, which is about 0.6 mm in thickness relative to the rest of appendage 304. This minimal thickness (e.g., about 0.6 mm) will allow for more efficient contact between the charger (not explicitly shown) and the charging coil 354. The appendage 304 may have another recessed part 362 (FIG. 30) with a minimal thickness relative to the rest of the wall of the appendage 304 to allow for better transmission of the PD and LED of the oxygen sensor 360.

Figure 31:
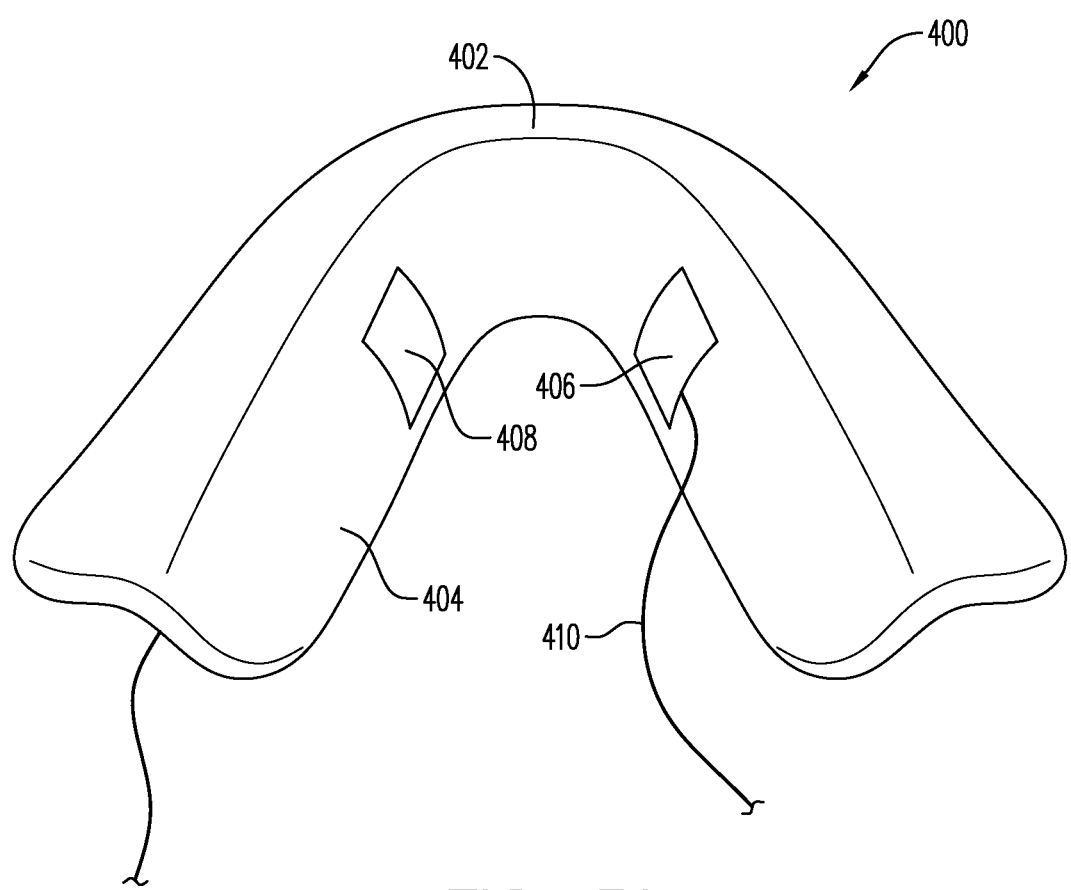
FIG. 31 is a bottom, perspective view illustrating an oral appliance including an electromyogram sensor according to another embodiment of the present disclosure.
Figure 32:
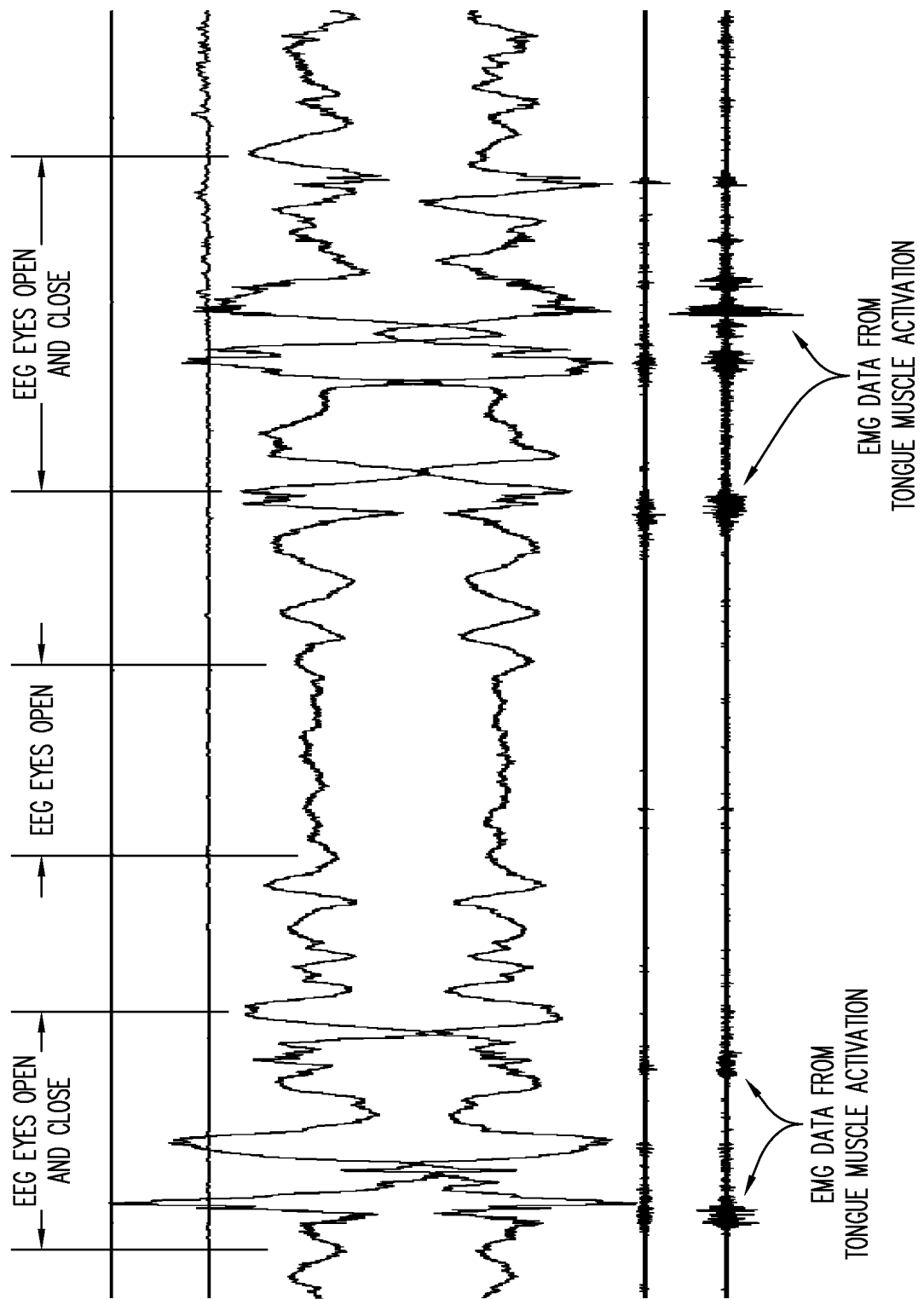
FIG. 32 is a chart illustrating electromyogram data collected during tongue muscle stimulation and while a user's eyes are moved between opened and closed configurations.

With reference to FIGS. 31-33, the present disclosure provides another embodiment of an oral appliance 400 for treating and/or collecting data used for treating sleep apnea. During sleep, electromyogram (EMG) can serve as an indicator of atonia (temporary paralysis of the user's legs and arms) while in REM vs non-REM sleep. It is contemplated that the oral appliance 400, which includes an EMG sensor, can provide data that would be indicative of respiratory events and arousals from apnea, and bruxism during sleep disturbances. EMG activity in subjects with sleep disorders may be typically more than twice as many as those without sleep disorders. It is contemplated that measuring the EMG of a user's intra-oral muscles may provide more sensitive and accurate data sets compared to external muscle EMG such as on the chin or the tibia.

The tongue is the largest and most active muscle in the oral cavity. It is also the upper respiratory muscle which is most involved in controlling air flow to the back of the throat during sleep. Hence, detecting its contractility during sleep can provide valuable physiological data for monitoring and diagnostic purposes. Because of the tongue's important role in respiration, detecting its electric activity during obstructive sleep apnea is valuable. The contemplated oral appliance 400 may be configured to detect such activities by placing EMG sensors along the right and left sides of the inferior-lateral aspects of the tongue while coupled to a removable mouthpiece. It is contemplated that the EMG sensor may partially or fully cover the anterior and posterior of the user's tongue, detecting the expiratory and inspiratory motor units associated with muscle fibers of the user's tongue.

As illustrated FIG. 31, an exemplary oral appliance 400 includes a mouthpiece 402 configured for being positioned in an oral cavity of a user. According to an aspect, the mouthpiece 402 includes a lingual wall 404 configured for being placed adjacent the user's tongue. The mouthpiece 402 may be made according to any of the methods described above and from any of the materials described above. The mouthpiece 402 is configured to be positioned on the user's lower jaw or upper jaw.

The oral appliance 400 further includes a pair of electromyogram (EMG) EMG sensors 406, 408 (e.g., the MYO-WARE muscle sensor). The EMG sensors 406, 408 are configured to provide physiological data for monitoring and diagnosing obstructive sleep apnea. According to an aspect, the EMG sensors 406, 408 are configured to detect an electrical activity of the user's tongue. The electrical activity may be indicative of a muscle contraction of the user's tongue. The EMG sensors 406, 408 are configured to be in contact with right and left sides of the user's tongue such that the EMG sensors 406, 408 detect twitches or contractions of the user's tongue bilaterally. The EMG sensors 406, 408 may be disposed on the mouthpiece 402 such that the EMG sensors 406, 408 contact the right and left sides of the inferior-lateral aspects of the user's tongue. It is contemplated that the EMG sensors 406, 408 may be sized so that they contact a partial area of the side(s) of the user's tongue. According to an aspect, the EMG sensors 406, 408 may be sized so that they can fully cover the anterior and posterior lateral surfaces of the user's tongue. It is contemplated that by being positioned to be in contact with the lateral surfaces of the user's tongue, the EMG sensors 406, 408 detect the expiratory and inspiratory motor units associated with muscle fibers of the user's tongue.

According to an aspect, the oral appliance 400 may include a single EMG sensor that contacts a single lateral surface of the user's tongue. Alternatively, multiple EMG sensors may be disposed on a single side of the mouthpiece 400 so that they all contact the same side (right of left lateral sides, for example) of the user's tongue. While FIG. 31 illustrates that the oral appliance 400 may include a wire 410 extending from the EMG sensors 406, 408, it is contemplated that the oral appliance 400 may be wireless.

According to an aspect, the oral appliance 400 may include a processor (not explicitly shown). The processor may include a micro-processor. According to an aspect, the EMG sensors 406, 408, in combination with the micro-processor, may be configured to identify respiratory events and arousals from obstructive sleep apnea. The EMG sensors 406, 408, in combination with the micro-processor, may be configured to identify bruxism during sleep disturbances.

The oral appliance 400 may further include a storage chip (not explicitly shown) configured to store and record data collected by the EMG sensors 406, 408. According to an aspect, a battery (not explicitly shown) may be provided to supply power to at least one of the EMG sensors 406, 408, the processor or micro-processor, and the storage chip. The battery may be a rechargeable battery. The oral appliance 400 may be positioned on a charger platform (not explicitly shown) so that the rechargeable battery can be charged so that it can supply power to the oral appliance 400.

When worn during sleep, the oral appliance 400 may provide information that serves as an indicator of at least one of atonia while the user is in REM sleep, respiratory events and arousals from apnea, and bruxism during sleep disturbances.

It is further contemplated that the oral appliance 400, in addition to the EMG sensor(s) 406, 408, may include an addition sensor (not explicitly shown). The additional sensor may be at least one of an oxygen sensor, a PPG sensor, or an inertial movement sensor. The EMG sensors 406, 408 and the additional sensor(s) may collectively gather physiologic data over time that aids in diagnosing obstructive sleep apnea. The micro-processor and rechargeable battery(s) may be sealed within the mouthpiece 400 or otherwise coupled to the mouthpiece 400.

Information or data gathered by the EMG sensors 406, 408 and the additional sensor(s) may be live streamed onto a smart device, for example, wirelessly via i.e., Bluetooth. The data can also be downloaded the next day by placing the appliance on a stationary hub/charger combination (not shown). The data can then be transferred onto a secure cloud based medium to be shared with the user as well as their care provider(s). The accumulation of this collective data may be built into a predictive model through deep thinking/artificial intelligence (AI) system integration to optimize the accurate diagnosis and subsequent monitoring of the ongoing treatment of patients suffering from sleep disordered breathing, i.e., obstructive sleep apnea. Additionally, the predictive model can assist in the determination of the most statistically efficacious prescribed therapy for OSA, with the highest probability of success, prior to the user engaging in any therapy which might provide sub-standard treatment response, such as positive air pressure (i.e., CPAP), custom oral sleep appliances, hypoglossal nerve stimulator, and pharmacotherapy.

It is contemplated that the EMG sensors 406, 408 may be suitably coupled to any of the oral appliances described herein.

The additional sensor coupled to the oral appliance 400 may be an EEG sensor. With reference to FIG. 32, EMG data was obtained using an EEG sensor to determine when a user's eyes are opened or closed: (Phase 1) the user's eyes were opened and then closed; (Phase 2) when the user's eyes were open; and (Phase 3) again, when the user's eyes were opened and then closed. During that test period, EMG data was gathered during Phase 1 and Phase 3. Distinct signals were obtained that reflected the electrical activity in the user's tongue.

FIG. 33 is a chart that illustrates the difference between EMG data representing tongue contraction and EMG data representing an absence of tongue contraction. As illustrated, distinct signals are obtained that reflect when there is muscle contraction or twitching of the user's tongue, which indicates the user is not in REM sleep whereas signals reflecting tongue muscle relaxation indicates the user is in REM sleep. No distinct signals were created during the absence of muscle contraction or twitching of the user's tongue.

The components of the apparatus illustrated are not limited to the specific embodiments described herein, but rather, features illustrated or described as part of one embodiment can be used on or in conjunction with other embodiments to yield yet a further embodiment. It is intended that the apparatus include such modifications and variations. Further, steps described in the method may be utilized independently and separately from other steps described herein.

While the apparatus and method have been described with reference to specific embodiments, it will be understood by those skilled in the art that various changes may be made and equivalents may be substituted for elements thereof without departing from the scope contemplated. In addition, many modifications may be made to adapt a particular situation or material to the teachings found herein without departing from the essential scope thereof.

In this specification and the claims that follow, reference will be made to a number of terms that have the following meanings. The singular forms "a," "an" and "the" include plural referents unless the context clearly dictates otherwise. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited to, "consisting essentially of" and "consisting of." Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. An oral appliance, comprising:
a mouthpiece configured to be positioned in an oral cavity of a user, the mouthpiece including:
an anterior wall configured to cover facial surfaces of the user's dentition;
a posterior wall configured to cover lingual surfaces of the user's dentition;
a transverse wall extending between the anterior wall and the posterior wall; and
an electronic assembly coupled to the mouthpiece, the electronic assembly including an oxygen sensor coupled to the anterior wall and configured to be oriented toward oral mucosa of the user's mouth to determine an oxygen saturation level of the user, the oxygen sensor comprising a light emitting diode (LED) and two or more photodiodes (PDs) in an arrangement, the LED configured to project both red and infrared lights, and each of the two or more PDs configured to detect reflections from the oral mucosa of at least a portion of both the red and infrared lights projected by the LED and generate photoplethysmography (PPG) data based on the reflections detected,
wherein the oxygen sensor is configured to detect reflections from the oral mucosa via the arrangement, wherein in the arrangement,
a first PD of the two or more PDs and a second PD of the two or more PDs are positioned on opposite sides of the LED,
a first centerline of the first PD, a second centerline of the second PD, and a third centerline of the LED are positioned in parallel,
the first PD has a major dimension extending along the first centerline and a minor dimension extending perpendicular to the first centerline such that the major dimension is larger than the minor dimension of the first PD,
the second PD has a major dimension extending along the second centerline and a minor dimension extending perpendicular to the second centerline such that the major dimension is larger than the minor dimension of the second PD, and
a distance between the first centerline of the first PD and the second centerline of the second PD is between 6 millimeters and 10 millimeters.

2. The oral appliance of claim 1, further comprising a housing positioned on the mouthpiece, wherein the housing includes, encompasses, or surrounds at least a portion of the electronic assembly.

3. The oral appliance of claim 1, wherein the electronic assembly further includes:
a printed circuit board; and
an optical housing supported on the printed circuit board, wherein the oxygen sensor is supported in the optical housing and electrically coupled to the printed circuit board.

4. The oral appliance of claim 1, wherein the oxygen sensor is a reflectance pulse oximeter configured to determine the oxygen saturation level of hemoglobin of the user via the reflections received by the two or more PDs.

5. The oral appliance of claim 1, wherein the electronic assembly has a first end portion coupled to the mouthpiece, and a second end portion configured to extend away from the mouthpiece in a direction toward gingiva of the user, the second end portion of the electronic assembly supporting the oxygen sensor thereon.

6. The oral appliance of claim 1, the electronic assembly including an electroencephalogram (EEG) electrode, wherein the EEG electrode is configured to be positioned adjacent the user's alveolar mucosa such that the EEG electrode detects brain wave signals.

7. The oral appliance of claim 1, further comprising a housing secured to the mouthpiece, opposite the transverse wall, wherein the housing defines an inner chamber of the mouthpiece; and
a microphone positioned in the inner chamber of the mouthpiece.

8. The oral appliance of claim 1, wherein a microphone is positioned on the mouthpiece and the microphone is covered by a semi-permeable membrane.

9. The oral appliance of claim 1, further wherein,
the mouthpiece comprises a first mouthpiece and a second mouthpiece;
the mouthpiece further comprising a strut including:
an elongate first portion having a first projection configured for receipt in a socket of the first mouthpiece; and
an elongate second portion extending perpendicularly from the elongate first portion and having a second projection configured for receipt in a socket of the second mouthpiece.

10. The oral appliance of claim 1, wherein the oxygen sensor is positioned above a top portion of the anterior wall.

11. The oral appliance of claim 1, further comprising an inertial measuring unit (IMU) coupled to the mouthpiece and configured to detect movement of the user.

12. The oral appliance of claim 1, wherein the electronic assembly includes a plurality of the oxygen sensors and each of the plurality of the oxygen sensors include a respective one of the LED and a respective two or more of the PDs.

13. An oral appliance, comprising:
a mouthpiece configured to be positioned in an oral cavity of a user, the mouthpiece including:
an anterior wall configured to cover facial surfaces of the user's dentition;
a posterior wall configured to cover lingual surfaces of the user's dentition;
a transverse wall extending between the anterior wall and the posterior wall; and
an electronic assembly coupled to the mouthpiece, the electronic assembly including an oxygen sensor coupled to the anterior wall and configured to be oriented toward oral mucosa of the user's mouth to determine an oxygen saturation level of the user and collect oxygen saturation (SpO2) and photoplethysmography (PPG) data, the oxygen sensor comprising a light emitting diode (LED) and two or more photodiodes (PDs) in an arrangement, the LED configured to project both red and infrared lights, and each of the two or more PDs configured to detect reflections from the oral mucosa of at least a portion of both the red and infrared lights projected by the LED,
wherein the oxygen sensor is configured to detect reflections from the oral mucosa via the arrangement, wherein in the arrangement,
a first PD of the two or more PDs and a second PD of the two or more PDs are positioned on opposite sides of the LED,
a first centerline of the first PD, a second centerline of the second PD, and a third centerline of the LED are positioned in parallel,
the first PD has a major dimension extending along the first centerline and a minor dimension extending perpendicular to the first centerline such that the major dimension is larger than the minor dimension of the first PD,
the second PD has a major dimension extending along the second centerline and a minor dimension extending perpendicular to the second centerline such that the major dimension is larger than the minor dimension of the second PD, and
a distance between the first centerline of the first PD and the second centerline of the second PD is between 6 millimeters and 10 millimeters.

14. The oral appliance of claim 13, further comprising an inertial measuring unit (IMU) coupled to the mouthpiece and configured to detect movement of the user.

15. The oral appliance of claim 13, wherein the electronic assembly has a first end portion coupled to the mouthpiece, and a second end portion configured to extend away from the mouthpiece in a direction toward gingiva of the user, the second end portion of the electronic assembly supporting the oxygen sensor thereon.

16. The oral appliance of claim 13, the electronic assembly including an electroencephalogram (EEG) electrode, wherein the EEG electrode is configured to be positioned adjacent the user's alveolar mucosa such that the EEG electrode detects brain wave signals.

17. An oral appliance, comprising:
a mouthpiece configured to be positioned in an oral cavity of a user, the mouthpiece including:
an anterior wall configured to cover facial surfaces of the user's dentition;
a posterior wall configured to cover lingual surfaces of the user's dentition;
a transverse wall extending between the anterior wall and the posterior wall;
an appendage configured to extend away from the anterior wall in a direction towards oral mucosa of the user's mouth and defining a space within the appendage; and
an electronic assembly including an oxygen sensor and positioned at least partially within the space within the appendage, wherein the appendage and electronic assembly are together configured for orienting the oxygen sensor toward the oral mucosa of the user's mouth, the oxygen sensor comprising a light emitting diode (LED) and two or more photodiodes (PDs) in an arrangement, the LED configured to project both red and infrared lights, and each of the two or more PDs configured to detect reflections from the oral mucosa of at least a portion of both the red and infrared lights projected by the LED and generate photoplethysmography (PPG) data based on the reflections detected,
wherein the oxygen sensor is configured to detect reflection from the oral mucosa via the arrangement, wherein in the arrangement,
a first PD of the two or more PDs and a second PD of the two or more PDs are positioned on opposite sides of the LED,
a first centerline of the first PD, a second centerline of the second PD, and a third centerline of the LED are positioned in parallel,
the first PD has a major dimension extending along the first centerline and a minor dimension extending perpendicular to the first centerline such that the major dimension is larger than the minor dimension of the first PD,
the second PD has a major dimension extending along the second centerline and a minor dimension extending perpendicular to the second centerline such that the major dimension is larger than the minor dimension of the second PD, and a distance between the first centerline of the first PD and the second centerline of the second PD is between 6 millimeters and 10 millimeters.

18. The oral appliance of claim 17, further comprising an inertial measuring unit (IMU) coupled to the mouthpiece and configured to detect movement of the user.

19. The oral appliance of claim 17, wherein the electronic assembly has a first end portion coupled to the mouthpiece, and a second end portion configured to extend away from the mouthpiece in a direction toward gingiva of the user, the second end portion of the electronic assembly supporting the oxygen sensor thereon.

20. The oral appliance of claim 17, the electronic assembly including an electroencephalogram (EEG) electrode, wherein the EEG electrode is configured to be positioned adjacent the user's alveolar mucosa such that the EEG electrode detects brain wave signals.

* * * * *